United States Patent
Catanzariti et al.

(10) Patent No.: US 9,545,200 B2
(45) Date of Patent: Jan. 17, 2017

(54) SYSTEMS AND METHODS FOR MAPPING THE OCULAR SURFACE

(71) Applicant: Precision Ocular Metrology, L.L.C., Cedar Crest, NM (US)

(72) Inventors: Scott P. Catanzariti, Cedar Crest, NM (US); Edwin J. Sarver, Cookeville, TN (US); Donald R. Sanders, Elmhurst, IL (US)

(73) Assignee: Precision Ocular Metrology, L.L.C., Cedar Crest, NM (US)

( * ) Notice: Subject to any disclaimer, the term of this patent is extended or adjusted under 35 U.S.C. 154(b) by 196 days.

(21) Appl. No.: 14/535,925

(22) Filed: Nov. 7, 2014

(65) Prior Publication Data

US 2015/0131055 A1 May 14, 2015

Related U.S. Application Data

(60) Provisional application No. 61/962,449, filed on Nov. 8, 2013.

(51) Int. Cl.
- *A61B 3/10* (2006.01)
- *A61B 3/107* (2006.01)
- *A61B 3/00* (2006.01)
- *A61B 3/14* (2006.01)

(52) U.S. Cl.
CPC ............. *A61B 3/107* (2013.01); *A61B 3/0025* (2013.01); *A61B 3/0041* (2013.01); *A61B 3/0091* (2013.01); *A61B 3/102* (2013.01); *A61B 3/14* (2013.01)

(58) Field of Classification Search
CPC ... A61B 3/0008; A61B 3/0025; A61B 3/0091; A61B 3/102; A61B 3/107; A61B 3/113; A61B 3/14

USPC ................ 351/205, 206, 210–212, 221, 246
See application file for complete search history.

(56) References Cited

U.S. PATENT DOCUMENTS

| | | | |
|---|---|---|---|
| 5,116,115 A * | 5/1992 | Lange | A61B 3/107 351/212 |
| 5,159,361 A | 10/1992 | Cambier et al. | |
| 5,873,832 A | 2/1999 | Maloney et al. | |
| 6,193,371 B1 * | 2/2001 | Snook | A61B 3/1005 351/212 |
| 6,613,041 B1 | 9/2003 | Schrunder | |
| 6,634,750 B2 | 10/2003 | Neal et al. | |

(Continued)

FOREIGN PATENT DOCUMENTS

WO 2015070006 A1 5/2015

OTHER PUBLICATIONS

International Preliminary Report on Patentability from corresponding International Patent Application No. PCT/US2014/064530, mailed May 19, 2016, in 14 pages.

(Continued)

*Primary Examiner* — Huy K Mai
(74) *Attorney, Agent, or Firm* — Knobbe, Martens, Olson & Bear, LLP

(57) ABSTRACT

Examples of methods and apparatus for an accurate measurement of the anterior surface of the eye including the corneal and scleral regions are disclosed. The measurements provide a three-dimensional map of the surface which can be used for a variety of ophthalmic and optometric applications from astigmatism and keratoconus diagnostics to scleral lens fitting.

33 Claims, 19 Drawing Sheets

(56) References Cited

U.S. PATENT DOCUMENTS

| | | |
|---|---|---|
| 7,111,938 B2 | 9/2006 | Andino et al. |
| 8,079,706 B2 | 12/2011 | Silvestrini et al. |
| 8,226,235 B2 | 7/2012 | Roberts et al. |
| 8,556,424 B2 | 10/2013 | Iwase et al. |
| 2008/0018856 A1 | 1/2008 | Sarver et al. |
| 2009/0275929 A1 | 11/2009 | Zickler |
| 2013/0083290 A1 | 4/2013 | Vinciguerra |
| 2013/0093998 A1 | 4/2013 | Bishop |

OTHER PUBLICATIONS

International Search Report and Written Opinion from corresponding International Patent Application No. PCT/US2014/064530, mailed Feb. 18, 2015, in 20 pages.

\* cited by examiner

SYSTEMS AND METHODS FOR MAPPING THE OCULAR SURFACE

CROSS-REFERENCE TO RELATED APPLICATIONS

This application claims the benefit of and priority to U.S. Provisional Patent Application No. 61/962,449, filed Nov. 8, 2013, entitled "SCLERAL TOPOGRAPHY MEASUREMENT DEVICE," which is hereby incorporated by reference herein in its entirety.

BACKGROUND

Technical Field

The present disclosure relates to three dimensional imaging using the structured light approach, and more particularly to ocular surface measurement over the anterior surfaces of the cornea and sclera.

Description of Related Art

The accurate knowledge of the corneal surface is very important for diagnostics and treatment of a number of ocular conditions. Cornea is responsible for about 70% of the refractive power of the eye and therefore the corneal topography has a great importance in determining the quality of vision. It is commonly used for diagnosis of keratoconus, for selecting appropriate soft contact lenses, for fitting scleral lenses, and for topography guided Laser-Assisted in situ Keratomileusis (LASIK).

Currently the majority of the corneal topography is performed using a Placido disk. The concept of the Placido disk was introduced by Antonio Placido in 1880 and since then it has been the primary method for corneal topography. The method is based on viewing or imaging the corneal reflection of series of concentric bright and dark rings positioned in front of the cornea. By increasing the number of concentric disks and placing them on a concave surface around the eye, it is possible to measure a large section of the cornea. But in most cases the data on the central zone needs to be interpolated and the data on the corneal periphery is often missing due to limited reflection. Additionally, Placido disks are not capable of measuring the scleral topography, which is important for custom fitting of scleral lenses.

In addition to the Placido disk, scanning slit systems, such as the Orbscan II by Bausch & Lomb, Scheimpflug systems such as the Galilei by Zeimer Ophthalmic Systems, and rastersterographic systems such as the CTS by Par Technlogies have been used for corneal topography. While these systems provide better measurement of the corneal apex they lack the coverage of the corneal periphery and sclera needed for scleral lens fitting.

SUMMARY

The present disclosure describes an advanced coded-light measurement system for mapping the complete three dimensional anterior ocular surface. Commonly used ocular topography measurements, including Placido-disk measurements, scanning slit beam measurements, and rastersterographic measurements have focused on the central region of the cornea. Extending such measurements to the entire anterior surface, specifically to include the sclera, introduces a new set of challenges. These include: the dissimilar optical properties of the sclera and the cornea, interference of the eyelids which can occlude significant portions of the desired measurement region even when manually retracted, and the periodic involuntary microsaccadic eye movements.

A sample embodiment of the technology disclosed herein provides a set of possible solutions that can be used together or independently to address one or more of the above challenges. In the said embodiment a single light projector is positioned to direct light towards the ocular surface and two or more imaging sensors are positioned to image the eye surface.

In the said embodiment the surface of the eye is coated with a fluorescent dye and the projector is configured to project light in a wavelength that overlaps the excitation band of the said dye. The resulting fluorescent light emitted from the dye covering the ocular surfaces is detected using imaging sensors. Using the above fluorescent imaging method solves the complication of dissimilar reflective properties of scleral and corneal surfaces.

In the said embodiment the projected light is comprised of coded light sequence. This sequence contains series of structured light patterns which can be interpreted as time-series measurements, where the projected intensity at a given location over time has a unique pattern for each pixel or subregion of pixels, allowing accurate, unambiguous identification of triangulation points in each member of the stereo-photogrammetric pair. Said triangulation measurements performed in order to obtain the three dimensional surface of the eye can be performed between two cameras or between one of the cameras and the projector. The above-mentioned triangulation measurements can be performed separately or in any combination of the above in order to increase measurement redundancy and reduce the measurement errors. Said coded-light sequences allow higher resolution measurements than conventional raster-stereographic methods by coding all pixels in the pattern region, instead of requiring interpolation between grid lines or grid intersection points.

In conventional coded light mapping of a surface topography a care is taken so that the measured object does not move during the measurement. Microsaccadic movements are involuntarily movements of the eye that occur once or twice every second. Therefore, it is advantageous to take these movements into account during the three dimensional mapping of the eye. One embodiment of the disclosed technology uses multiple wavelength illumination of the eye during the structured light imaging. One wavelength can be used for excitation of the fluorescent dye during coded light imaging, while another wavelength or wavelengths can be selected so the features on the eye surface, including but not limited to the blood vessels and limbus can be resolved in the recorded images. The said light of different wavelengths can be projected onto the eye simultaneously or in sequence. In one embodiment of the disclosed technology the light of the said wavelengths can be projected before and after the coded light sequence. In said embodiment locations of the ocular surface features in the images before and after the projection of the coded light can be compared to ensure that eye did not move during the measurement and the data set can be used for three dimensional surface reconstruction.

Embodiments herein allow for measurement of the complete anterior ocular surface, including regions which may be occluded by the eyelids even when said eyelids are retracted manually, by combining multiple measurements of the ocular surface taken for different gaze directions of the eye. Each of said multiple measurements produces a partial surface model of the visible region of the ocular surface, including three dimensional surface coordinates and color or intensity measurements. Feature information from the color or intensity component of the model is used to aid convergence of the model registration processes, allowing the smooth surfaces of the multiple said partial surface models to be uniquely registered in space into a complete model of the full anterior ocular surface.

In other implementations, the object being mapped need not be a human or animal eye and may be any other type of surface. The disclosed systems and methods may be advantageous for mapping a surface of a moving or unstable object (biologic or non-biologic).

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any disclosures described herein, which are defined solely by the claims attached hereto.

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure.

DETAILED DESCRIPTION

The present disclosure is directed toward systems and methods for performing surface measurement, mapping, and modeling of the complete anterior surface of the eye, including the corneal and scleral regions of the eye.

Figure 1A:
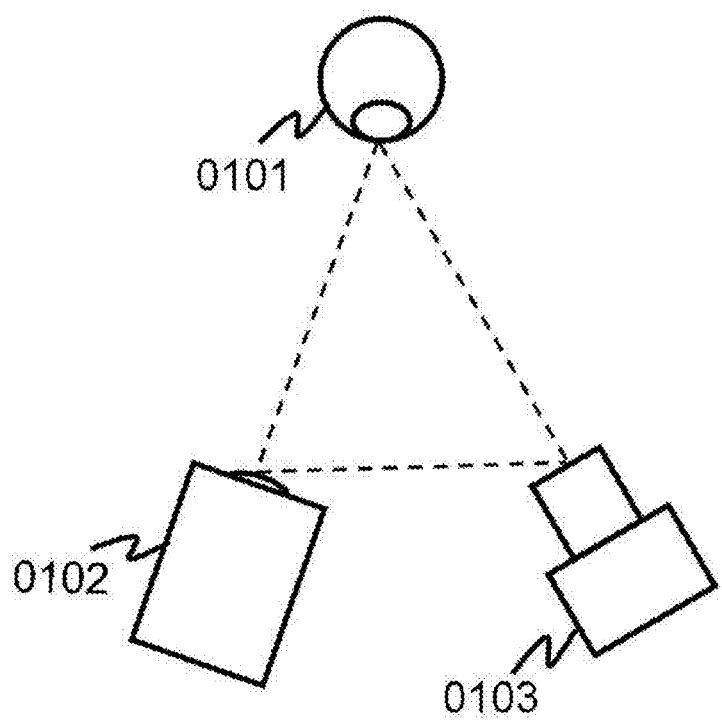
FIG. 1a is a schematic illustration of an example of a stereo-photogrammetric triangulation between single camera and single projector
Figure 1B:
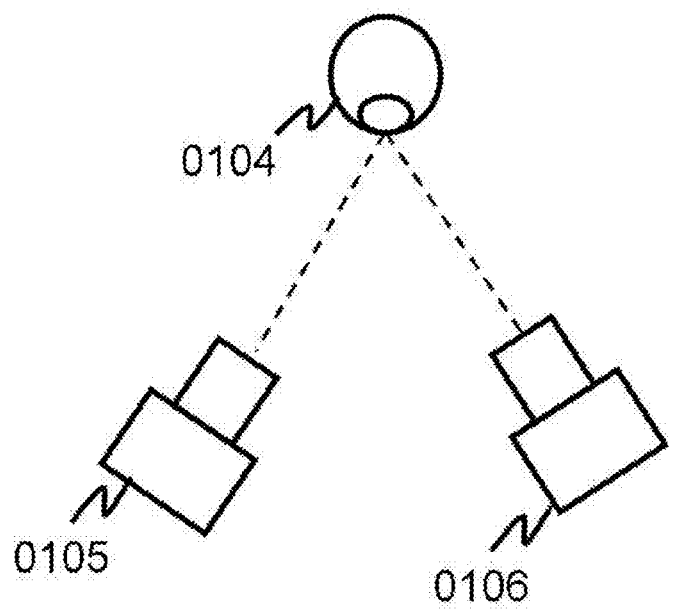
FIG. 1b is a schematic illustration of an example of a stereo-photogrammetric triangulation between two cameras.

Commonly use ocular topography measurements have focused on corneal topography and include: Placido disk measurements which using concentric illuminated rings to map the surface slope and infer topography elevation measurements from the slopes based on specific assumptions, scanning slit measurements which use using moving laser line or slit beam triangulation methods to calculate the elevation topography, and rasterstereographic measurements which triangulate points from a static pattern projected on the ocular surface and interpolate between the triangulated points. Scanning slit and rasterstereographic methods typically employ stereo-photogrammetric measurement pairs which may comprise a light-source 0102 and an imaging detector 0103 with known orientations relative to the surface to be measured 0101, as depicted schematically in FIG. 1a, or may comprise two imaging detectors 0105 and 0106 with known orientations relative to the surface to be measured 0104, as depicted in FIG. 1b. Calibration of the stereo-photogrammetric pairs allows accurate triangulation of points in three dimensional space from the two-dimensional locations of the points in the imaging planes of the respective light source or imaging detectors.

Figure 2:
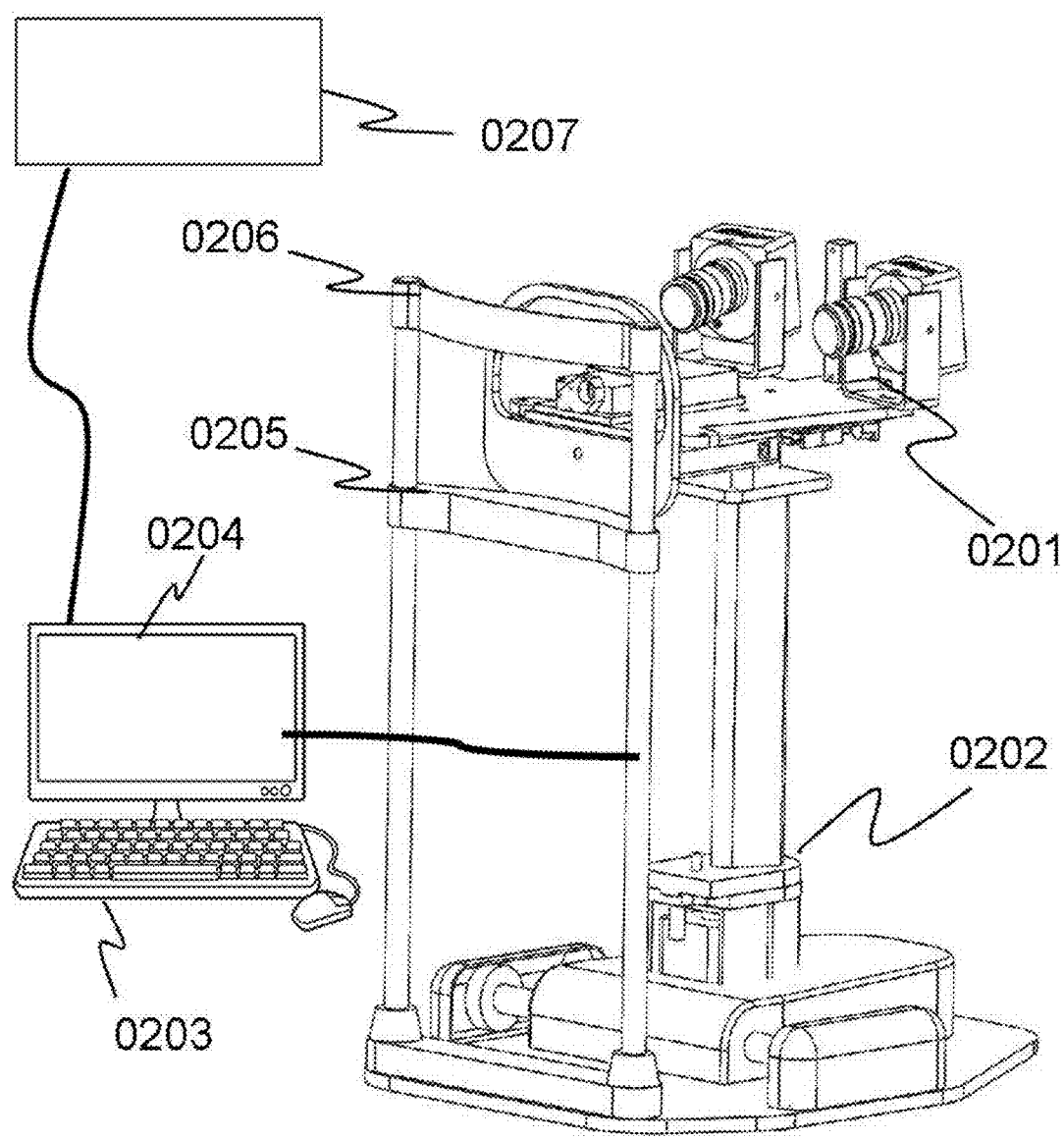
FIG. 2 is an illustration of an example of a system for measuring the ocular surface.

According to some embodiments of the technology described herein, a system for mapping and modeling of the ocular surface can include an optical measurement head comprised of a pattern projection system, two cameras, and a fixation target array for fixing the gaze direction of the subject during the series of measurements, a mounting system for the optical measurement head comprising a mounting stand attached to manipulator with a chin and forehead rest for controlling the relative orientations of the eye of the subject to be measured and the optical measurement head, a computing device connected to the measurement head for controlling measurement acquisition and processing the acquired data, and a display screen. FIG. 2 shows the schematic drawing of one embodiment of the technology described herein, including an optical head 0201, a manipulator comprising a moveable optical stand 0202, a chin rest 0205, a forehead rest 0206, an attached computing device 0203, and a display screen 0204 (which may include computer processing hardware configured to implement the analysis methods disclosed herein). Optionally, in some embodiments, the technology can be in communication with a scleral contact lens manufacturing system 0207, which can utilize information related to the topographic map of the eye generated by the technology for diagnosis or customized treatment of the subject's eye or for manufacturing of a scleral contact lens for the subject's eye. The scleral contact lens manufacturing system 0207 can be geographically remote from the rest of the system, and the topographic map information can be communicated to the manufacturing system 0207 via a network connection (e.g., the Internet, a local or wide area network, etc.).

Figure 3:
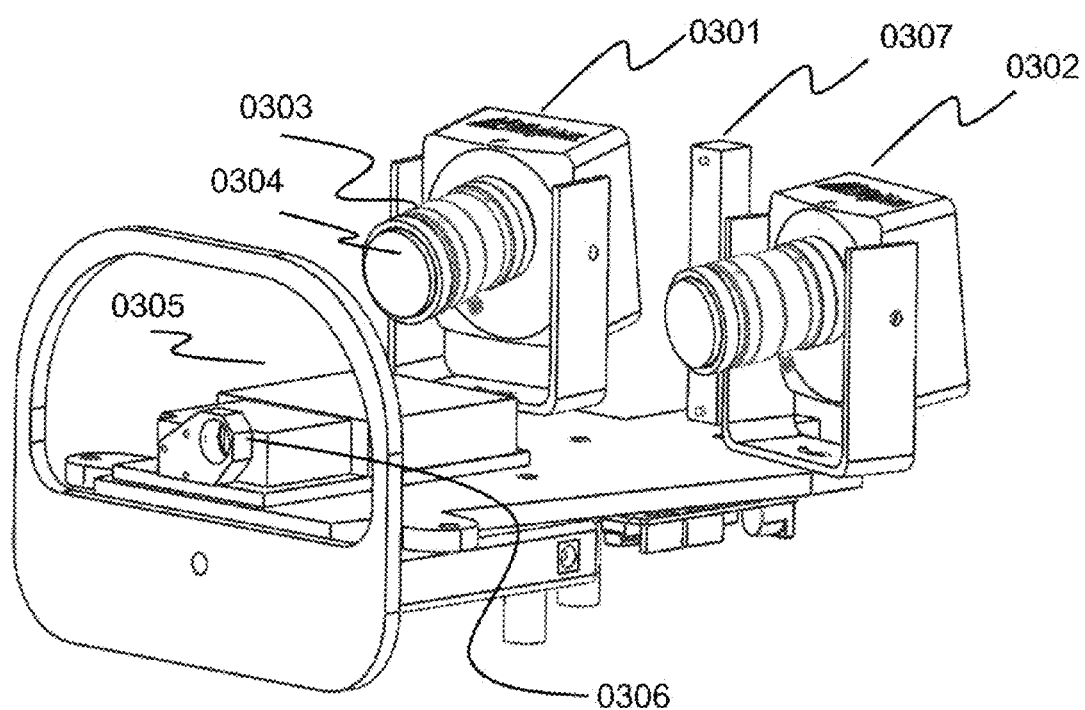
FIG. 3 is an illustration of an example of an optical head arrangement

FIG. 3 shows the internal structure of one embodiment of the optical measurement head. Referring now to FIG. 3, the pattern projection system comprising a digital light processing (DLP) or liquid crystal device (LCD) projector 0305 and an optical beam-shaping assembly 0306 is located in front of the eye so that the surface of the eye is within the focusing depth of field of the projected pattern image. In other embodiments, any type of micro-mirror device, microelectromechanical system (MEMS) device, or spatial light modulator can be used. A series of structured light patterns are projected onto the surface of the eye, wherein the tear film is stained with a fluorescing substance such as fluorescein. The pattern projection system produces structured light patterns and flat-field illuminations in at least two wavelength bands, chosen such that in some wavelength band the projected wavelength range overlaps with the excitation wavelength of the fluorescent substance but not the fluorescence wavelength of said fluorescent substance, and in another wavelength band the projected wavelength range overlaps the fluorescence wavelength of the fluorescent substance but not the excitation wavelength of said fluorescent substance. This is achieved by either utilizing optical filters in the projection optical path or by using a narrow wavelength multi-LED (light emitting diode) light source within the projector, where at least one LED in the multi-LED light source corresponds to each of the required wavelength bands previously described. The projection of a structured light pattern onto the anterior surface of an eye stained with said fluorescent substance results in fluorescence of the eye surface in accordance with the incident structured light pattern projection. This fluoresce is imaged using two charge coupled device (CCD) or complementary metal-oxide-semiconductor (CMOS) cameras 0301 and 0302 positioned at a certain angle on each side of the projector. The focusing depth of field of the camera optics is chosen to correspond with focusing depth of field of the pattern projection system optics so that a clear image of the fluorescence grid lines on the anterior ocular surfaces is obtained. In this embodiment, the optical system of each camera 0303 includes a fluorescence emission filter 0304, which allows imaging the fluorescence signal without the interference from the reflected portion of the excitation light that is output by the projector. Camera operation is synchronized with the projector output so that one or more images are recorded by each camera for each of the frames in the projected structured light pattern sequence. In some embodiments, illumination levels incident on the ocular surface are less than $3.9 \times 10^{-3}$ Joules of radiant energy as measured through a 7-mm aperture located within 5 mm of the projector focus.

Figure 4:
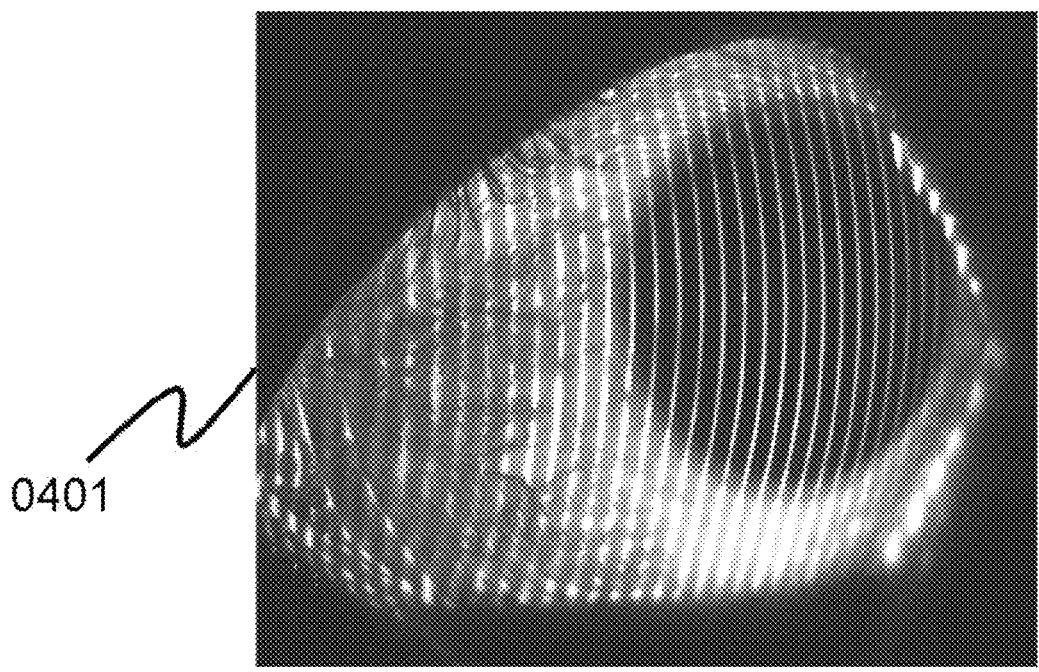
FIG. 4 includes example images of the structured light illuminated eye treated with fluorescein dye.
Figure 4:
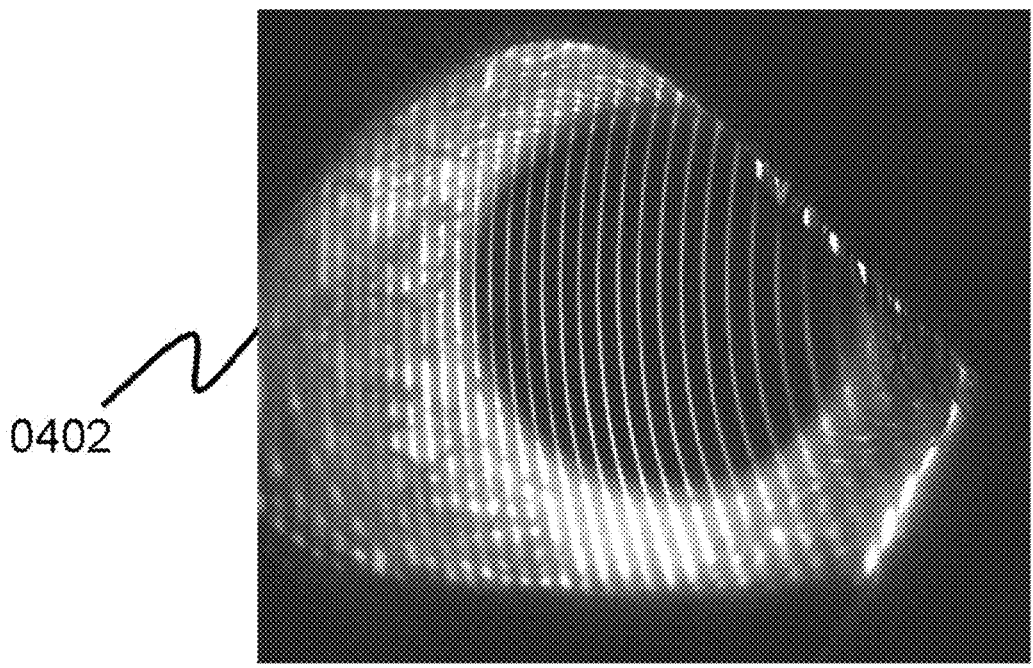

In one embodiment described herein the projected structured light pattern sequence is comprised at least in part of a series of interchanging vertical and horizontal grids of parallel lines. FIG. 4 shows the sample fluorescence images resulting from projecting said grids onto the eye surface. The images presented are recorded by the two cameras in the optical measurement head, one of which is located on the right side of the optical axis of the projector 0401 and the other located on the left side of the optical axis of the pattern projection system 0402.

Figure 5A:
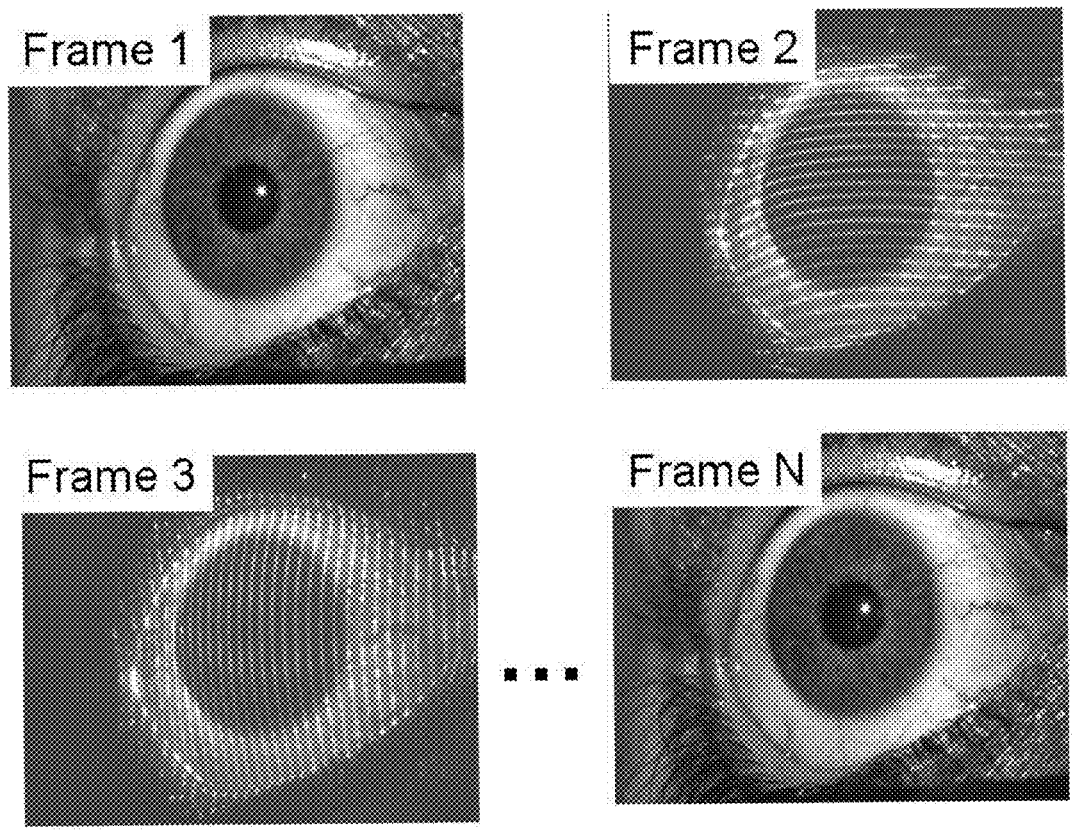
FIG. 5a includes example images illustrating one possible structured light illumination sequence incorporating flat-field frames for a measurement system operating in Discrete Station Mode FIG. 5b includes example images illustrating a possible structured light illumination sequence incorporating flat-field frames for the measurement system operating in Continuous Processing Mode
Figure 5B:
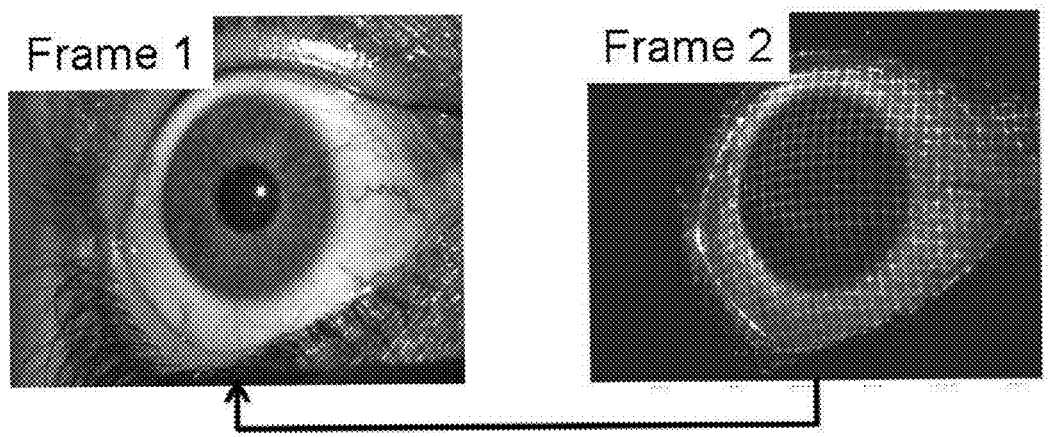

In some embodiments of the technology described herein, the projected structured light pattern sequence also comprises additional flat-field frames which may precede the projected structured light pattern grids, follow them, or both. In these flat-field frames the eye is illuminated by a uniform or almost uniform light with a wavelength that overlaps the transmission wavelength of the fluorescence emission filter located in the optical path of the cameras but does not overlap the excitation wavelength of the fluorescent substance introduced into the tear film. A single image or several images are recorded by each camera during the said flat-field illumination of the eye. In some embodiments, these emission wavelength flat-field illumination images recorded before and after an excitation wavelength sequence of projected structured light patterns can be used to verify that the eye has not moved during the measurement and for correction of measurement artifacts caused by any such eye movement. Since it has been reported that the microsaccadic movements of the eye involuntarily occur with a periodicity between 0.3 and 1 seconds it can be advantageous that the entire measurement sequence should last less than about 0.5 second. In embodiments where multiple frame structured light sequences are employed, emission wavelength illumination imaging can be used to verify that the eye hasn't moved during the measurement sequence. A sample sequence of images showing flat-field emission wavelength illumination images bracketing a sequence of several excitation wavelength structured light illumination images is presented in FIG. 5*a*.

In some embodiments, the structured light sequence duration can be shortened by projecting multiple illumination patterns simultaneously in non-overlapping wavelength bands, employing color imaging systems, and employing hardware and software filtering to isolate each pattern in the processing. In such embodiments, the structured light sequence duration can be as short as a single camera frame, typically five milliseconds or less.

Some embodiments can be used for mapping the surface of the eye in order to create a custom back surface of the scleral lens for a comfortable fitting. For said application it can be advantageous that a measurement of the ocular surface is performed within a 12 mm to 22 mm diameter circle centered at the cornea apex. For such large diameters the portions of the scleral and corneal surfaces may be hidden behind the eyelids, therein complicating the measurement procedure.

Figure 6:
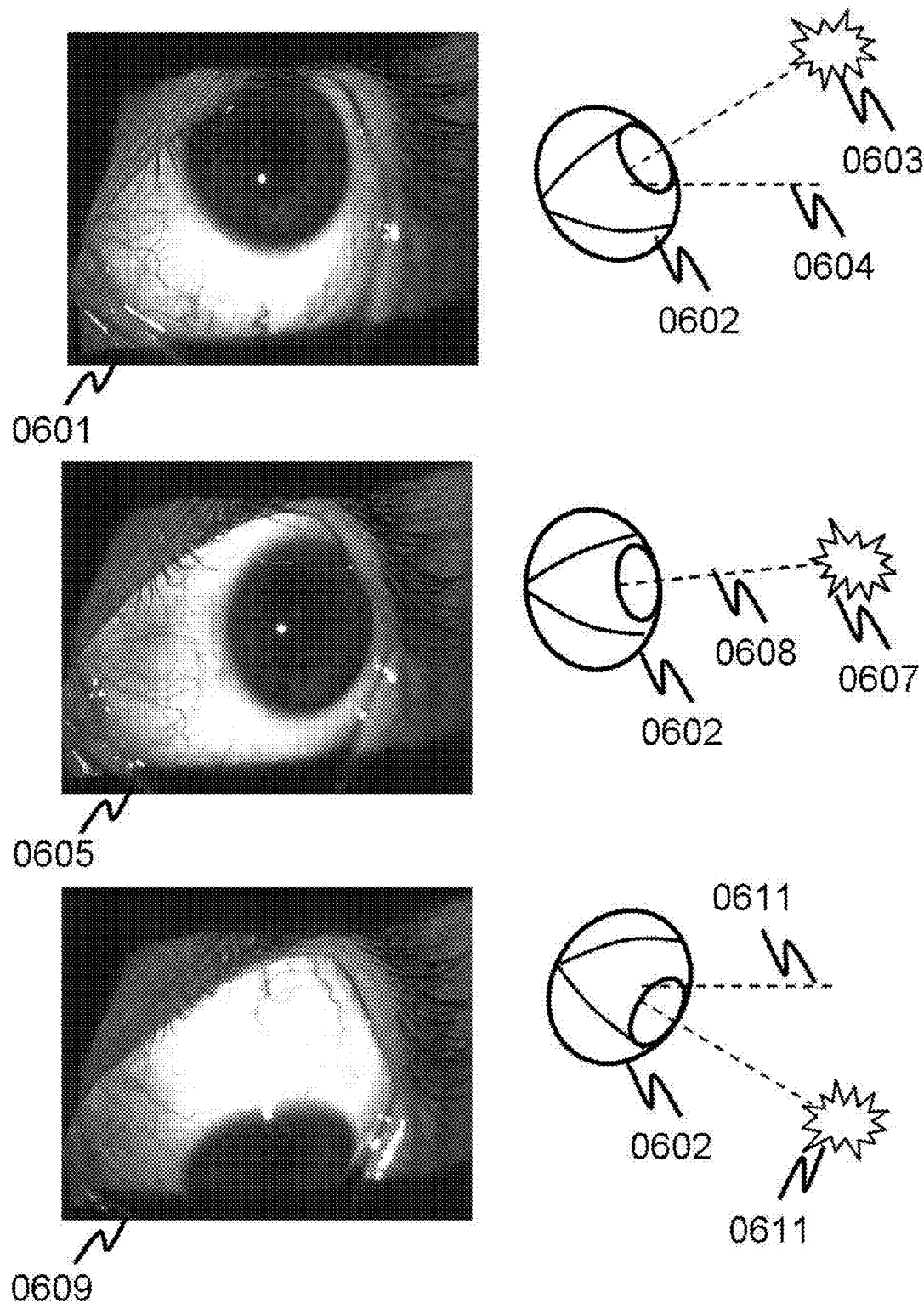
FIG. 6 is an illustration of use of fixation targets to acquire data for multiple gaze directions for the purpose of mapping the ocular area under the eyelids

In some embodiments, a fixation target array can be used to guide the gaze direction of the subject during the surface measurement process such that measurements are taken with the eye oriented at each of a plurality of gaze directions, such that each measurement comprises data of a different portion of the ocular surface. In said embodiments the location of each element in the fixation target array is chosen so that there is a significant overlap between measurements that can be used for later manual or automated stitching of the plurality of measurements in order to obtain a single composite model of the eye surface within 12 mm to 22 mm diameter region centered at the corneal apex, which may include regions of the ocular surface normally hidden by eyelids. FIG. 6 depicts a measurement process comprising measurements of the eye 0602 fixed at three gazed directions corresponding to three different illuminated elements in the gaze fixation target array 603, 607, 611. Flat-field illumination images captured at each gaze direction are depicted in 0601 0605 and 0609.

In the abovementioned embodiments the manual or automated registration and stitching of the resulting three dimensional datasets taken at each gaze direction can be performed either by optimizing correspondence between the three dimensional shapes and features in each dataset as measured using fluorescence wavelength illumination, or by combining said optimization of correspondence with three dimensional shapes with color or monochrome intensity feature information for optical surface features such as the corneal limbus and blood vessels obtained during flat-field illumination.

Figure 7:
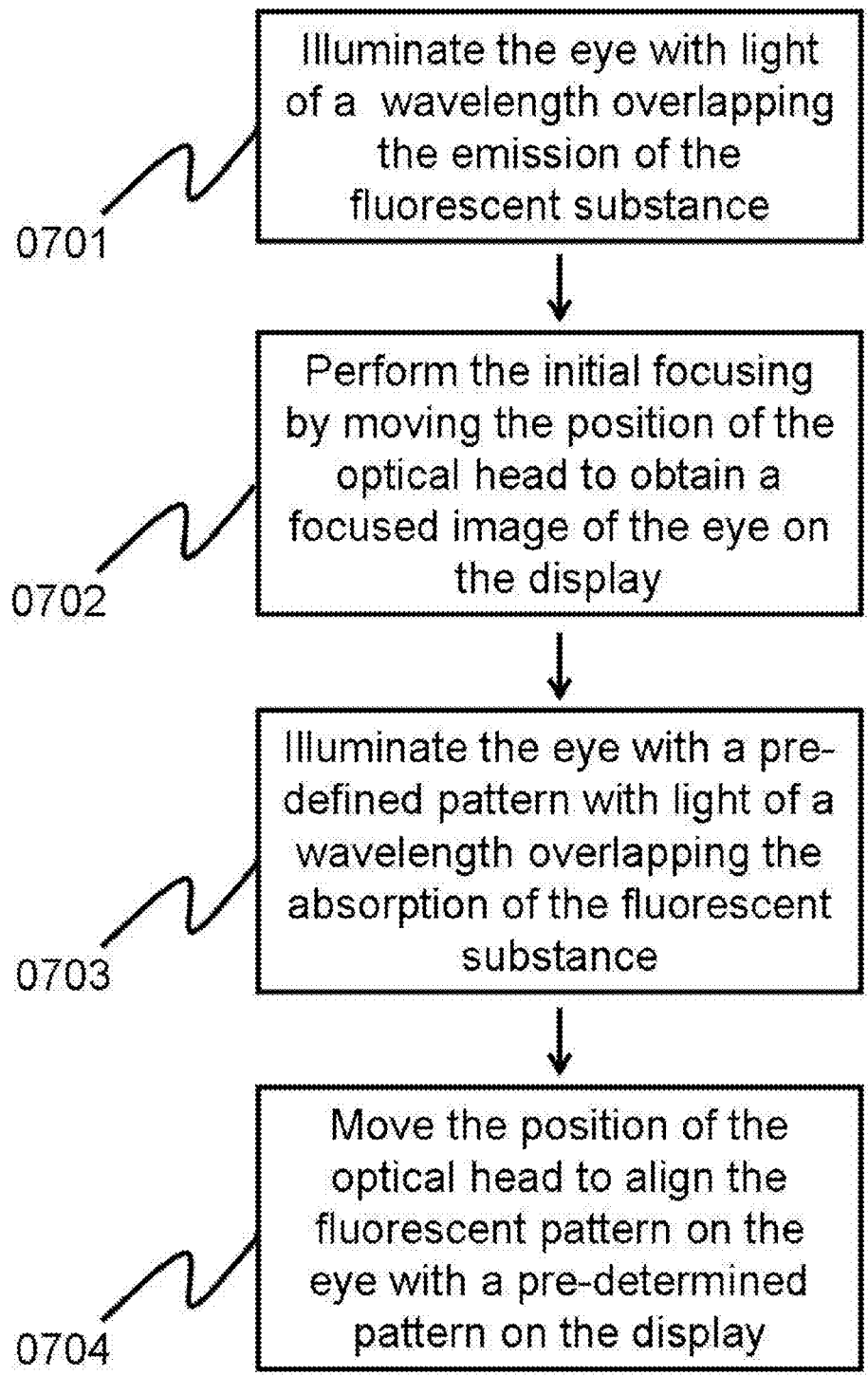
FIG. 7 is a flow chart illustrating an example focusing process

In some embodiments alignment and focusing can be achieved by providing the operator of the system with a real time display from one or more cameras during the manual focusing procedures. The focusing procedure can then be separated into two distinct steps. The sequence of these steps is described in FIG. 7. In the first stage the eye is illuminated with a dim light 0701 with the wavelength overlapping the emission wavelength of the fluorescent substance and the transmission wavelength of the bandpass filter installed in the optical path of the camera. During this stage the eye image is viewed on the display and is centered and focused in the camera field of view by manually adjusting the position of the optical measurement head using the manipulator 0702. In the second step a cross or other focusing pattern is projected by the projector 0703 operating in the wavelength of the fluorescence excitation of the fluorescing substance that was used to dye the tear film and the eye surface. As the position of the optical measurement head is adjusted by means of the manipulator, the location of focusing pattern in the fluorescence image of the eye shifts in the camera's vision frame, and hence on the display screen. The physical position or the optical head is adjusted forward or backward 0704 until the apparent position of this fluorescence focusing pattern on the display screen overlays a corresponding fixed focusing guide pattern which is also displayed on the device screen. When the fluorescence image focusing pattern and the fixed focusing guide pattern are co-located on the display screen, the eye is correctly centered in the optical depth of field of all relevant optical systems. Additional confirmation of the focusing state is provided to the operator by means of variations in color of the fixed focusing guide pattern. This procedure allows for fast, very accurate focusing of the eye for the performance of the mapping procedure.

In some embodiments the intensity of the fluorescence can be evaluated during or after the focusing process and a visual or auditory indication can be used to alert the operator of the state of the fluorescent dye on the ocular surface. In the case of insufficient dye the operator can be prompted to add more dye to the eye before continuing with the measurement.

During the operation of the device in all of the above-mentioned embodiments the intensity of the illumination for the fluorescence and emission wavelength is selected so that it does not exceed the safety limits established by appropriate standards.

In one embodiment described herein the pattern projection system can be capable of projecting one or more sequential predetermined two-dimensional patterns, whereas first and second cameras may be still or video CCD, CMOS or other cameras. The herein topography system comprises between one and three simultaneous stereo measurements.

In another embodiment, a method for aligning and focusing a topographic mapping device for an ocular surface of an eye of a subject is provided. The topographic mapping device can comprise a projection system, one or more imaging sensors and a display. The method comprises illuminating the eye with one or more structured alignment patterns, capturing reflected or fluorescence images of the one or more structured alignment patterns by the one or more imaging sensors, and displaying the reflected or fluorescence images in real-time on the display. Focusing of the topographic mapping device can be achieved by adjusting the device position such that a visible pattern in the reflected or fluorescence image of the structured alignment pattern visually aligns with a corresponding guide pattern which is displayed along with the captured reflected or fluorescence images on the display. The display can show indicators like color changes, text instructions, audio cues, etc. to instruct or inform the focusing and alignment process. In some embodiments, the method can include simultaneously or sequentially illuminating the eye with two distinct focusing patterns including a flat-field illumination and a structured alignment pattern. In some such embodiments, the method can include visually aligning the device using images of the reflected flat field illumination. In some embodiments, the flat field illumination is projected in a wavelength range that overlaps a fluorescence wavelength of a fluorescent dye used to prepare the ocular surface of the eye but does not overlap an excitation wavelength of the fluorescent dye, and the structured alignment pattern is projected in a wavelength range that overlaps the excitation wavelength of the fluorescent dye used to prepare the ocular surface but does not overlap the fluorescence wavelength of the fluorescent dye.

Figure 8:
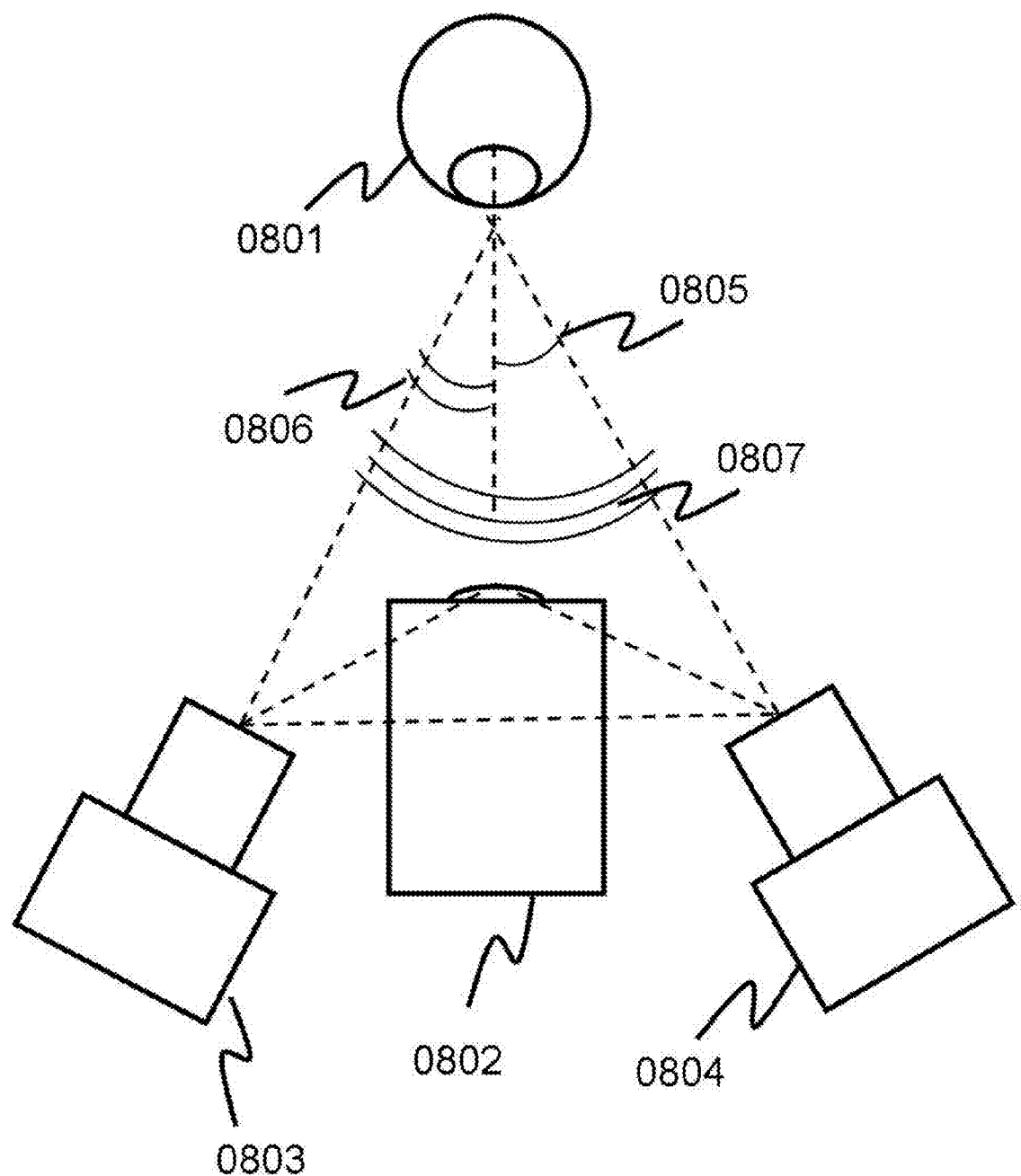
FIG. 8 is a schematic illustration of triangulation options offered by a multiple camera, single projector measurement arrangement.

In the example embodiment depicted in FIG. 8, the first camera 0803 and second camera 0804 can be arranged to form a stereo-vision pair with a field of view encompassing the illuminated portion of the surface to be measured 0801 Herein the illumination from the pattern projection system 0802 is used to index correspondence between each illuminated pixel in the first camera to each illuminated pixel in the second camera, and where a three-dimensional stereo calibration of the stereo pair can be used to triangulate the pixel correspondences between cameras into points in Cartesian space.

In said embodiment, the first camera 0803 and the pattern projection system 0802 can be calibrated to provide a coded light linked stereo pair, the pixel identities in the projected pattern as determined by the projected coded light sequence are indexed to the illuminated pixels in the first camera, and where a 3D structured light calibration between the pattern projector and the first camera can be used to triangulate the matched pixels between the projector and the camera into points in Cartesian space.

In said embodiment, the second camera 0804 and the pattern projection system can be calibrated to provide a coded light linked stereo pair, the pixel identities in the projected pattern as determined by the projected coded light sequence are indexed to the illuminated pixels in the second camera, and where a three-dimensional structured light calibration between the pattern projector and the second camera can be used to triangulate the matched pixels between the projector and the camera into points in Cartesian space.

In said embodiment, between one and three abovementioned stereo measurement methods can be used simultaneously to provide between one and three distinct measurements of the ocular surface. The obtained measurements can then be combined, averaged, or otherwise mathematically manipulated in order to increase the measurement accuracy at the entire measurement region or at a specific portion of the ocular surface. For example, the triangulation between the projector and the right camera can be used for measurement of the right side of the eye and the triangulation between the projector and the left camera can be used for measurement of the left side of the eye, while the triangulation between the two cameras can be used for the central portion of the eye, and overlap between the measurement regions can be used to achieve error reduction.

Several other embodiments can be made by adding capabilities, features, or by changing the ocular target to other objects with potentially varying surface topographies.

Figure 9:
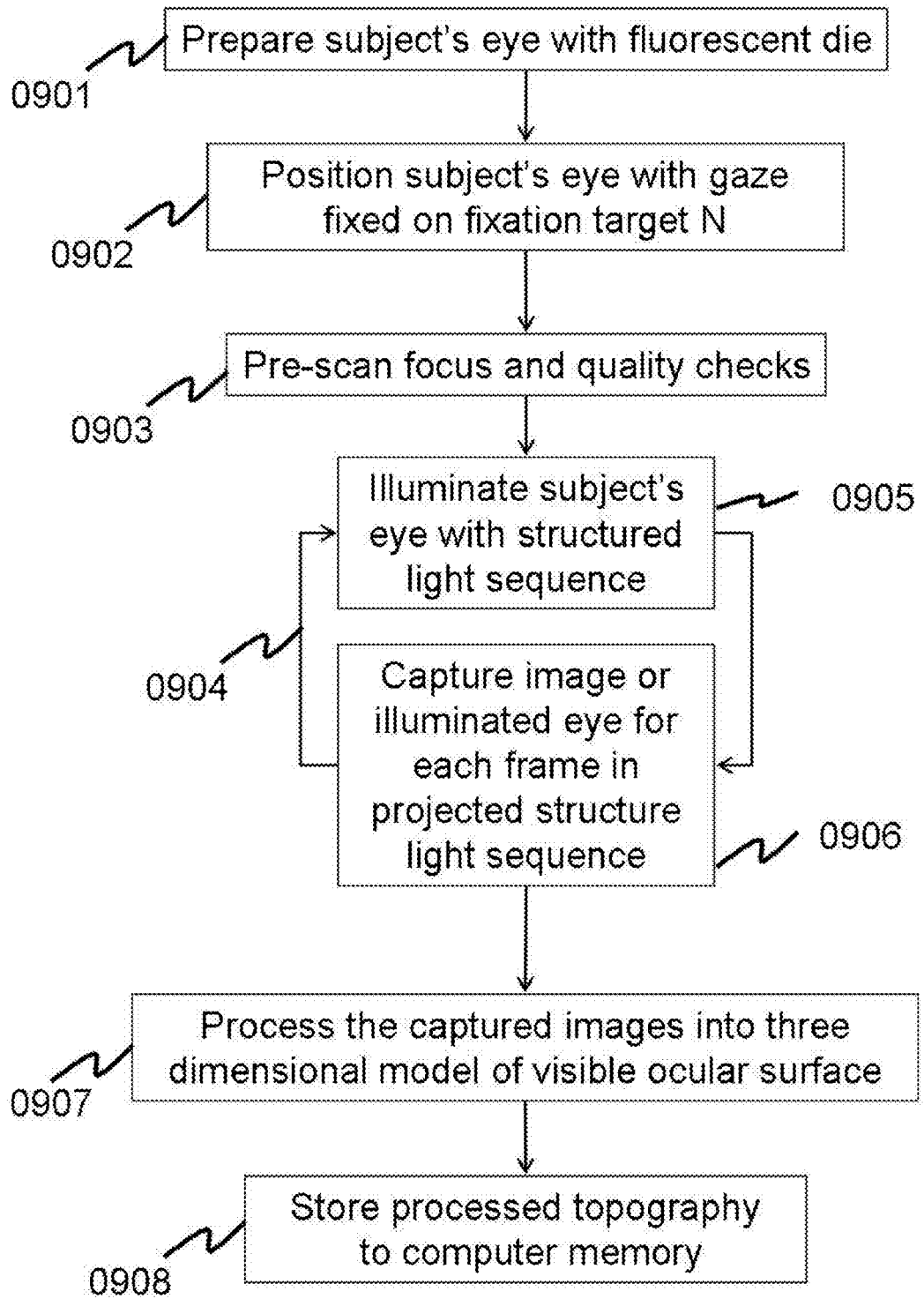
FIG. 9 is a flow chart illustrating an example data acquisition process.

The measurement process for the some embodiments is depicted in FIG. 9, wherein the subject's eye is prepared with fluorescent dye 0901 and positioned with respect to the optical head 0902. The computing device then calculates and checks focus and data quality metrics 0903 before initiating the formal data acquisition. Formal data acquisition takes the form of a loop 0904 wherein a frame of the structure light pattern sequence is projected onto the ocular surface 0905 and the emitted or reflected light from the ocular surface is captured by each imaging detector 0906 and transferred to the controlling computing device. At the conclusion of the formal data acquisition loop, the acquired images are processed into three dimensional topographical models of the anterior ocular surface 0907. These three dimensional topographical models are then stored in the memory of the computing device 0908 and may subsequently combined with other measurements or used to calculate optometric data products of various types.

In some embodiments the sequence of structured light patterns is comprised in part by a series of one or more two-dimensional coded light patterns which allow specific pixels or regions in the projected pattern or combination of patterns to be indexed to specific pixels or regions in images of the ocular surface taken under illumination by said coded light pattern or combination of patterns.

Figure 10:
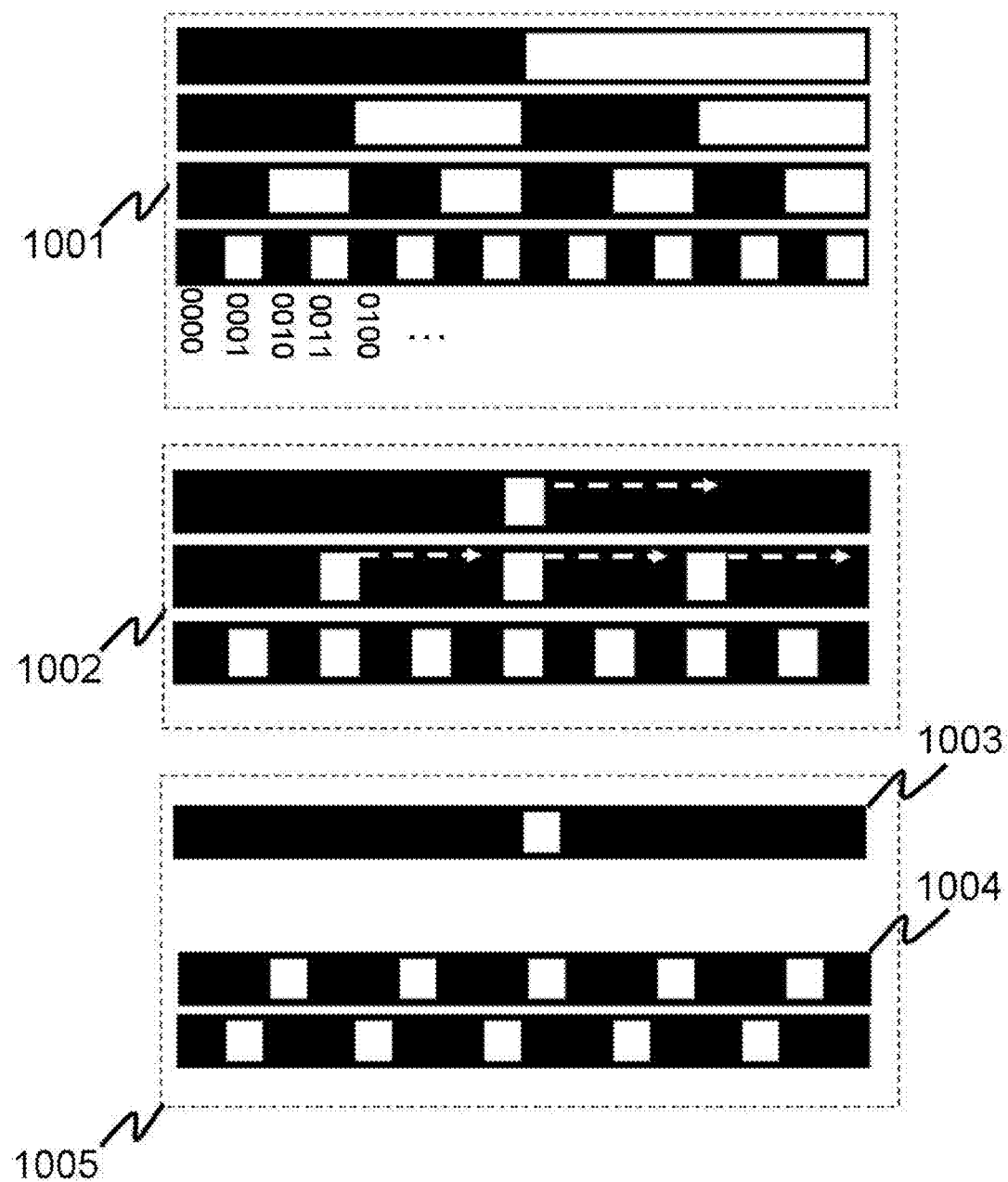
FIG. 10 is an illustration of sample coded light encoding sequences

Combinations of coded light patterns may uniquely encode each row and column of the projector pixel array, or may uniquely encode tiled portions of the projector pixel array in a repeating manner and rely on knowledge of surface constraints such as smoothness and continuity to allow unique pixel codes to be established from repeating series. An example of the former approach is the traditional binary encoding scheme 1001 depicted in FIG. 10, where a square wave pattern of ON=1 and OFF=0 values is projected and each pattern in the sequence increases the frequency of the pattern by a factor of two until the square wave pattern has a wave period of just two pixels. By examining the time-series values at each pixel for the entire sequence, a unique code value is achieved for each pixel in the array.

An example of the latter approach can be a series of N frames containing a 2-d array of parallel stripes oriented along the columns of the pixel array, and where every Nth column has value ON=1, and all other pixels in the frame have value OFF=0. If for each subsequent frame in the sequence the columns are shifted forward by one pixel, by projecting the N frames and examining the time series values of the pixels for each column, it is apparent that the first N columns have unique values, and then for the next N columns, the first N values repeat, and this repetition continues for each set of N columns until the far edge of the pixel array is reached. That is, for any given column code value, there can be many columns in the pixel array that share that code. For surfaces with known constraints such as smoothness, continuity, radius limit, and the like, this ambiguity can be dealt with algorithmically. As illustrated in the example in 1004 using N=3, if the stripes in a given frame are located on every Nth pixel, it is not strictly necessary to project N frames, but rather N−1 frames are sufficient as a sequence of all zeroes represents a valid code sequence. The advantage of such an approach is to take advantage of computing power to limit the number of frames in the coded light sequence without sacrificing measurement resolution. As depicted in 1005, the addition of a key stripe frame 1003 can be used in addition to surface constraints to further limit the ambiguity inherent in the encoded repeating series.

Another encoding scheme similar to the traditional binary approach can be used by projecting narrow stripes instead of bar or square wave patterns, as illustrated in 1002. In such an approach the same period increases between frames can be used, and each column can again be uniquely encoded provided the surface is relatively smooth and continuous with only minor algorithmic steps by using the stripes of the N−1th image in the sequence to locate those in the Nth image. The advantage of this type of encoding scheme over the traditional binary encoding scheme, or a comparable Gray Code approach, using bar or square wave patterns of increasing frequencies is that it minimizes the required dynamic range of the imaging detector by flattening the intensity of the illumination incident on the ocular surface, preventing blooming of illuminated features in the imaging detector and increasing the measurement speed by eliminating the need to dynamically adjust the exposure and aperture values of the imaging detectors during the measurement process.

In some embodiments the encoding schemes are based on grids of parallel lines which shift in space on the projector frame during the encoding process. Such encoding sequences can be parallel vertical lines and parallel horizontal lines in sequential or alternating series where the shifting vertical lines are used to encode the column values and the shifting horizontal lines are used to encode the row values. Or the encoding sequence can be a shifting Cartesian grid composed of parallel vertical lines and parallel horizontal lines superimposed on the same pattern frame. In the latter case, the horizontal and vertical components of the pattern can be isolated algorithmically via Fourier methods.

In some embodiments, regions of the projector pixel array are uniquely encoded and these regions repeat in a tiled pattern across the entire pixel array, which are algorithmically decoded in to unique code values for each individual pixel as required by some of the surface reconstruction methods described subsequently. The robustness of the decoding process by which the repeating tiled pixel code sequence is transformed into a set of unique pixel codes for each and every pixel in the array can be greatly enhanced by the use of a key stripe pattern during the coded light sequence projection, which guides the algorithm—a Templated Grid Search.

Figure 11A:
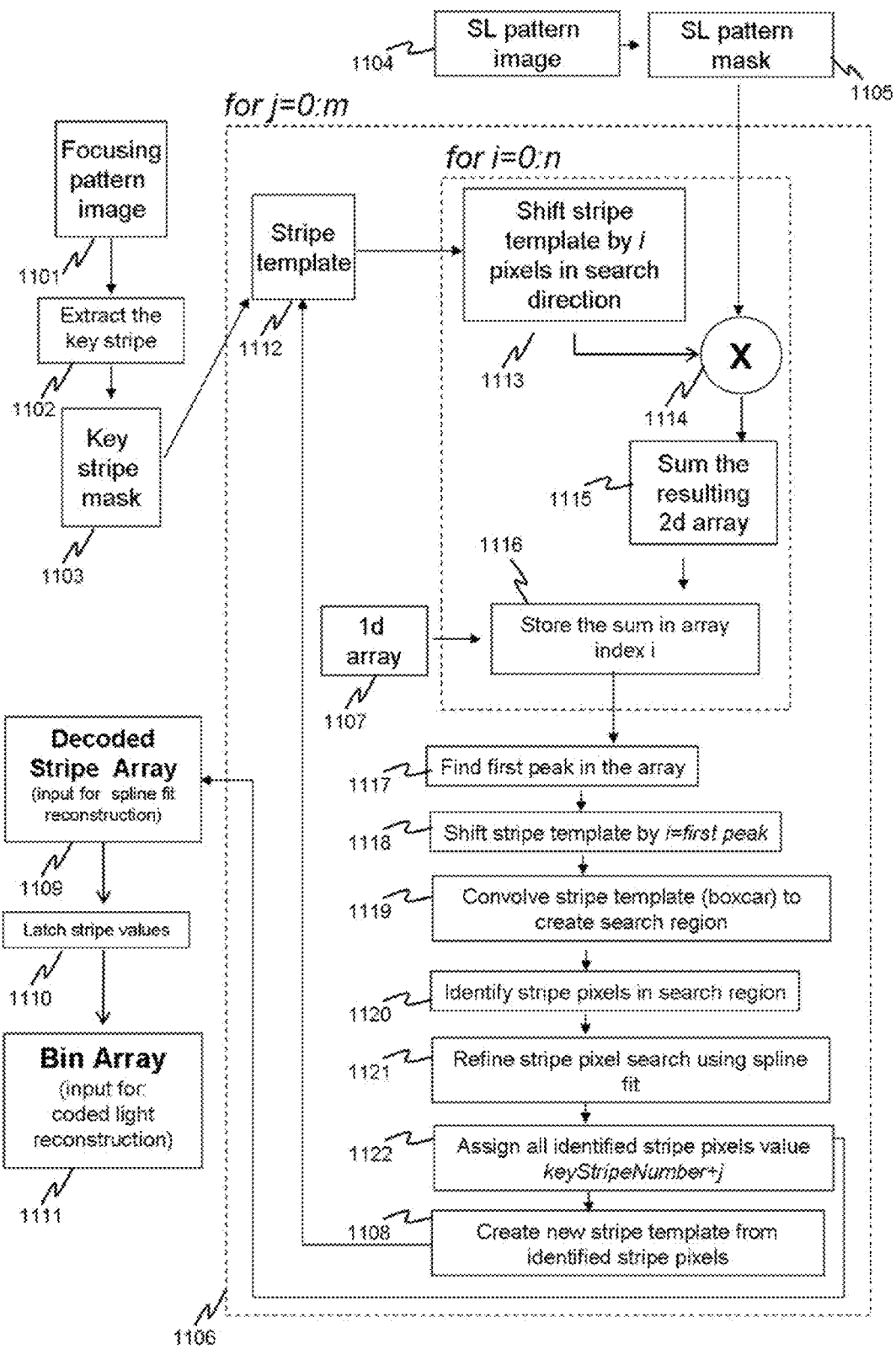
FIG. 11a is flow chart depicting an example of a templated grid search algorithm.
Figure 11B:
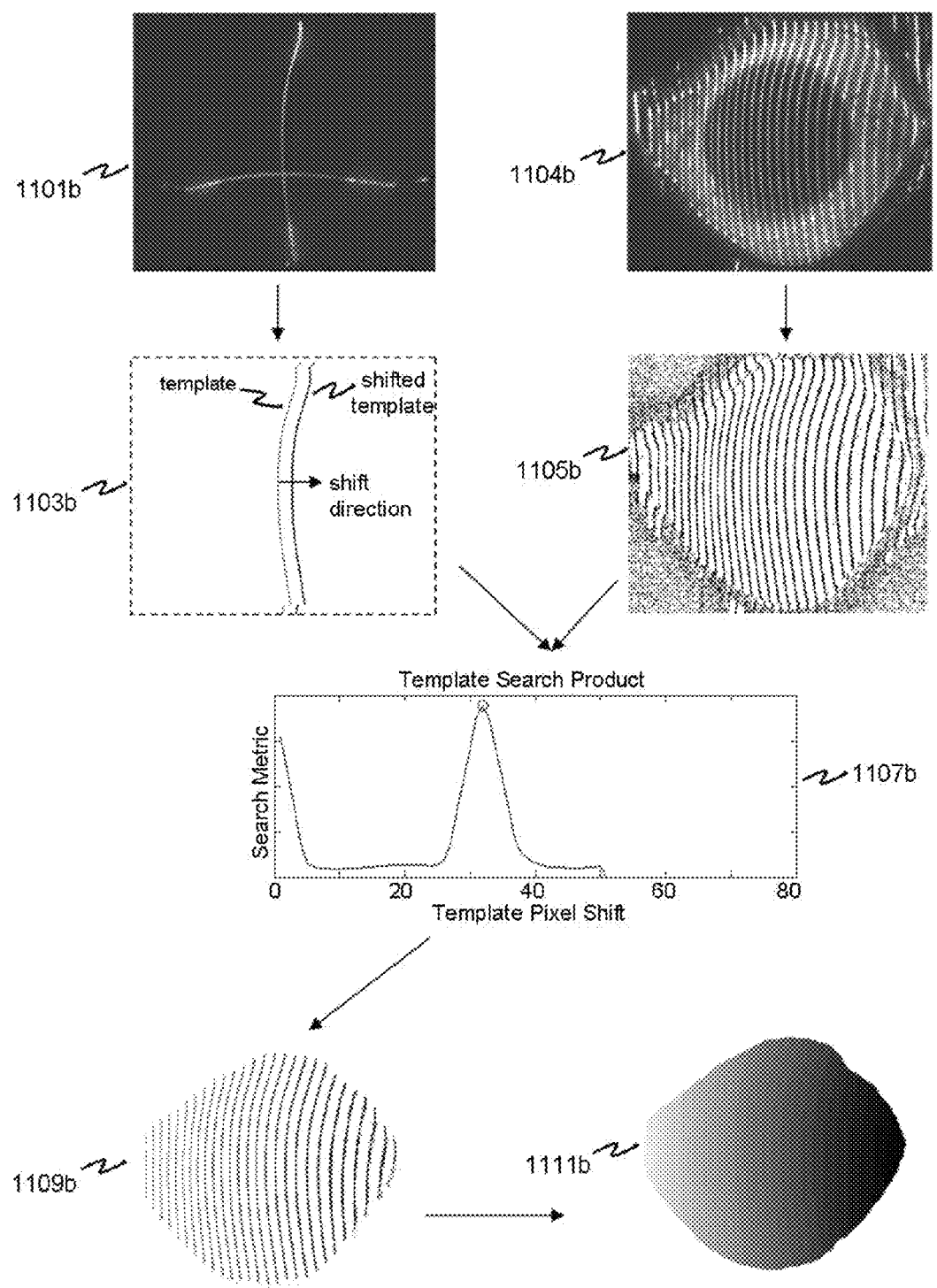
FIG. 11b is an illustration of examples of data products at various stages in a sample templated grid search.

In the Templated Grid Search, an example of which is depicted in the flowchart in FIG. 11a, a two-dimensional key mask 1103 is produced from a focusing pattern or key stripe image 1101 captured by illuminating the ocular surface with a structured light key stripe pattern. This key stripe pattern is applied algorithmically to a structured light pattern mask 1105 produced from an image captured by illuminating the ocular surface with a structured light pattern composed of parallel lines 1104, where the key stripe image represents a subset of this second structured light pattern. The key stripe mask is used as a template by which neighboring stripes in the sequence can by identified and numbered with their appropriate row or column value. Simply, the key stripe mask is shifted in space in a loop 1106 wherein the product between the shifted key stripe mask and the structured light pattern mask observed for subsequent shifts and recorded in an array 1107. When the product of these two images passes through a local maximum, the neighboring stripe in the parallel grid is reached, and the pixels in said neighboring stripe can be identified using the shifted key stripe mask as a template to define the search area. The newly identified stripe 1108 then becomes the key stripe which is used as the template to find the next stripe over, in a continuing fashion. Each newly found stripe is assigned a unique stripe number in a modified version of the structure light pattern mask 1109, which can then be converted into the bin array 1111 through simple value latching. This approach allows the algorithm to easily overcome gaps and intensity variations in fluorescein coverage and similar data faults. The approach is also very robust for a wide variety of surface topologies with no foreknowledge of the surface properties, allowing wide latitude in the positioning and orientation of the target surface in the field-of-view of the measurement system. FIG. 11*b* provides examples of the key stripe image 1101*b*, the extracted key stripe template 1103*b*, the structured light illuminated eye 1104*b*, and the structured light pattern mask 1105*b*. The key stripe template 1103*b* is iteratively shifted and applied to the structured light mask 1105*b*, and the search product 1107*b* is evaluated to determine the location of the next stripe. The gray scale intensity in the resulting masks 1109*b* and 1111*b* illustrate the decoded stripe numbering.

In some embodiments, the encoding scheme of the coded light patterns is chosen to maximize processing flexibility in the surface reconstruction algorithms. It can be advantageous for the encoding scheme to uniquely encode the projector array pixels or pixel subregions in a manner that facilitates coded light calibration of each camera-projector stereo pair, which allows code-light triangulation and rasterstereographic triangulation methods to be employed for surface reconstruction. It is also desirable in some datasets to employ spline fit surface reconstruction methods which can leverage the column and row code values. Finally, by choosing parallel stripes with the proper periodicity, phase based square-wave reconstruction algorithms may also be employed. Each of these reconstruction techniques may be used alone or in combination with one or more of the others to reconstruct the surface of the desired three dimensional surface topography model.

Coded-light reconstruction refers specifically to the method of calculating three dimensional surface points from a series of structured light patterns which, when analyzed in its entirety, uniquely defines the relationship between the pixels of the projected array and the three dimensional measurement region in which the ocular surface is situated. It can be performed by treating the pattern projection array as an inverse camera and triangulating between the pattern projection array and a given imaging detector. In this reconstruction method, a set of calibration coefficients is generated which uniquely define the relationship between a ray of light projected from a given pixel in the pattern projection system pixel array and the two dimensional pixel array of the imaging detector, enabling algorithmic definition of three-dimensional points in space from the two-dimensional pixel coordinates of the imaging detector when combined with the pixel code information that uniquely encodes the pattern projection system pixels.

Rasterstereographic reconstruction relies on direct triangulation between two cameras which are calibrated as a stereographic pair, generating a set of calibration coefficients that uniquely defines the relationship between the pixel coordinates of an incident light ray in camera 1 and the pixel coordinates of an incident ray in camera 2 which come from the same surface point in three dimensional space. In this reconstruction approach the encoding sequences of the projected coded light patterns are used to index pixel correspondence between the two cameras in the stereographic pair, that is, to demonstrate that the light incident at one location in camera 1 came from the same point on the surface as the ray of light incident at a second location in camera 2.

Slit-spline based surface reconstruction can be applied to any combination of the structured light patterns used in the coded light structured light pattern sequence, including operations on single image frames. This reconstruction technique may be applied using either or both of the camera-projector stereo-calibration used in the coded light reconstruction approach and the camera-camera stereo calibration used in the rasterstereographic reconstruction approach. In the slit-spline approach, the Templated Grid Search is used to uniquely identify the structured light pattern features evident in a single image frame. Spline fits to the pattern features are then combined with one or more of the stereo calibrations to create a surface representation of the anterior ocular surface. When applied to full sets of captured coded-light image sequences, the slit-spline method is used to constrain and refine the results obtained from the coded-light and rasterstereographic reconstructions. When the coded-light dataset is interrupted by motion of the eye during the measurement, the slit spline reconstruction approach can be applied to subsets of the captured image sequence to mitigate errors introduced by the ocular motion.

Phase-shift surface reconstruction uses Fourier analysis to measure the phase offsets between corresponding pixels in imaging elements of the stereo pairs. It can be used equally in conjunction with the camera-projector stereo calibration used in the coded light reconstruction method and to the camera-camera calibration used in the rastersterographic reconstruction. The parallax phase differences between the two imaging elements are used to calculate the three dimensional surface coordinates, and can be applied to single images, allowing it to be used to rescue datasets during which the eye has moved during the projected pattern sequence. Additionally, for measurements containing a sequence of shifted phase-shifted square-wave patterns where the eye remains stable during the measurement process, the phase-shift approach has the advantage of offering resolution beyond the pixel or row limits of the projected patterns (see Brenner 1999), so it can be applied as supplemental processing to the coded-light and rasterstereographic reconstruction methods to refine the model surfaces.

Figure 12:
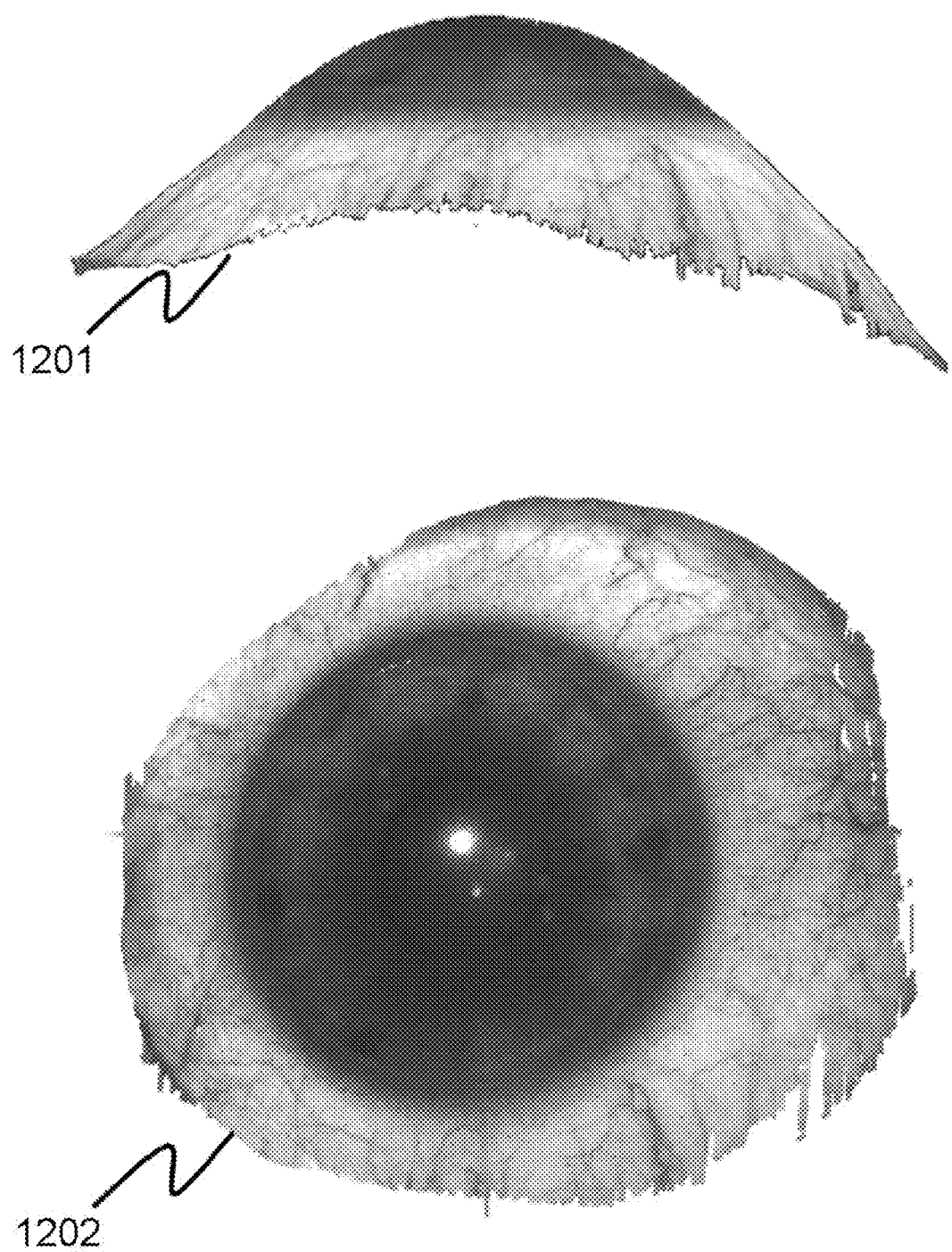
FIG. 12 is an example of the measured 3D surface of the eye surface obtained by manually retracting the eyelids

In one embodiment, a full three dimensional topographical model of the anterior ocular surface can be obtained from a single measurement taken with the gaze direction of the eye fixed on a single fixation point. In this embodiment the lids of the eye are retracted manually by the practitioner to expose the desired extent of the scleral and corneal regions of the anterior surface to be imaged. FIG. 12 shows a sample map of the eye surface recorded with the eyelids mechanically retracted, viewed in profile 1201 and from a point on the optical axis 1202

In other embodiments, a full three dimensional topographical model of the anterior ocular surface is created as a composite model from a plurality of individual three dimensional topographical models of the anterior ocular surface where each individual three dimensional topographical model is calculated from a measurement taken with the eye fixed on each of a plurality of fixation points.

In one such embodiment, registration of the various topography models is accomplished using feature information gleaned from flat-field illumination of the eye captured in conjunction with the coded light patterns. This can be done before or after using emission wavelength, or can be done simultaneously by using non-overlapping light source and color camera.

In said embodiment Scale Invariant Feature Transform (SIFT) and Block Match (BM) algorithms are used to identify features on the scleral surface and create a feature based description of each model which orients it in space. Comparison of component features in each feature based model description allows direct registration of models with respect to one another. An iterative registration algorithm is then used to refine the fit, where X,Y,Z components, and feature proximity are all used as optimization parameters.

Figure 13:
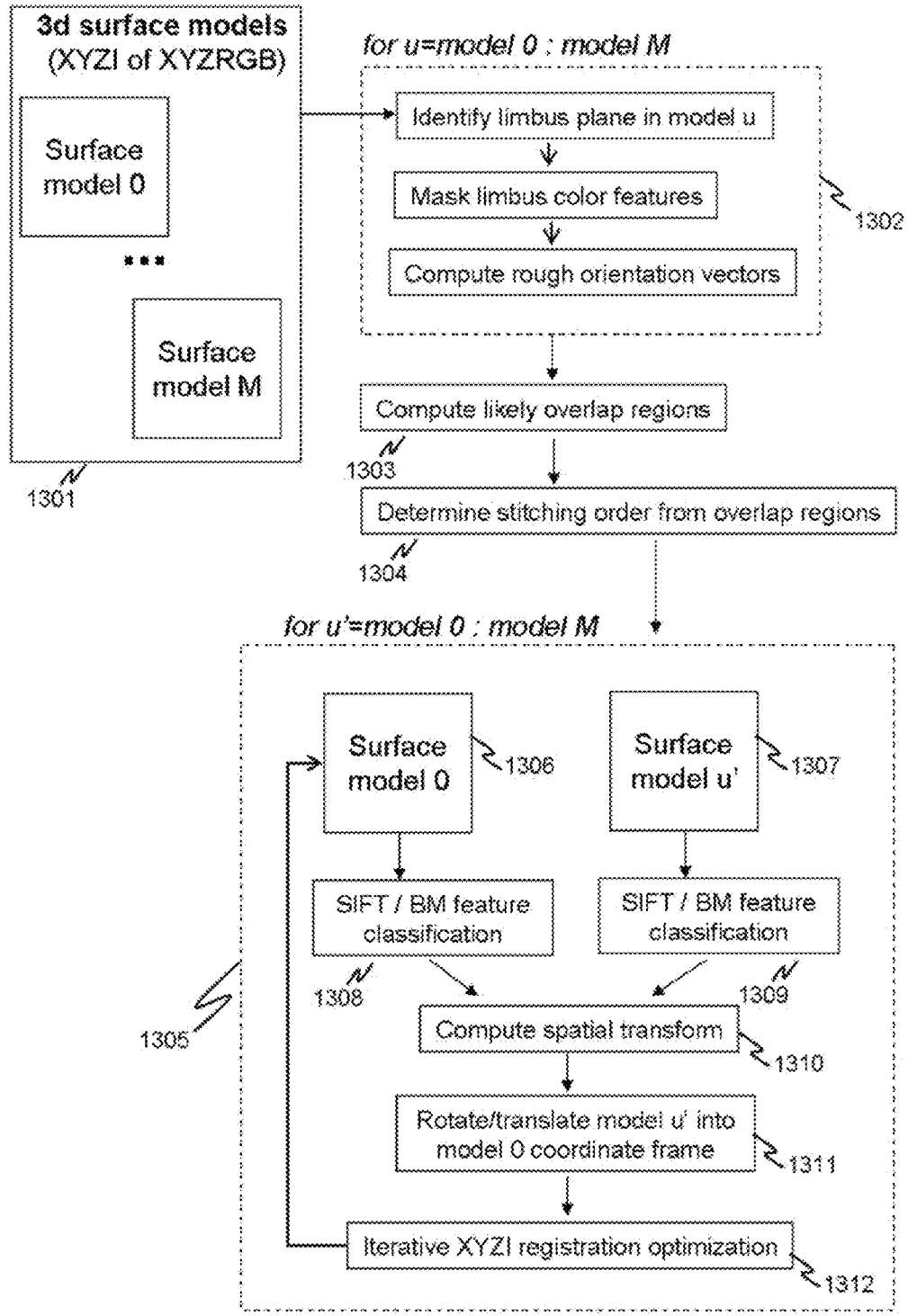
FIG. 13 is a flow chart depicting a sample stitching algorithm for combining three dimensional surface models obtained at multiple gaze directions for the purpose of mapping the surface of the eye under the eyelids.
Figure 14:
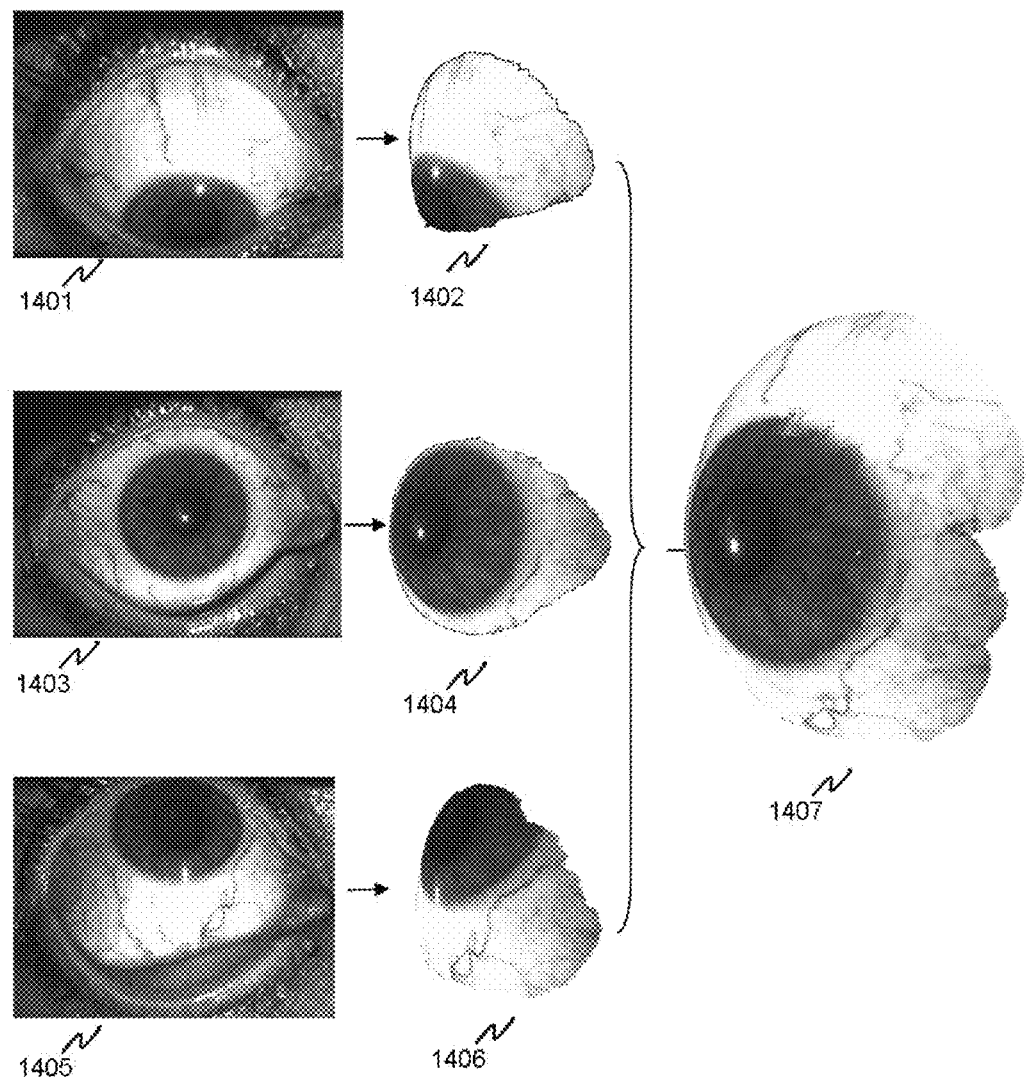
FIG. 14 is an illustration demonstrating examples of intermediate and final results of the stitching algorithm for mapping the surface of the eye under the eyelids.

The stitching registration process by which the individual three dimensional topography models are combined into a composite three dimensional topography model of the full extents of the anterior ocular surface is depicted in FIG. 13. Each of the series of individual three dimensional topography models 1301 is analyzed 1302 to compute a rough orientation vector, from which the estimated overlap regions between each model can be computed 1303, which are then used to determine the order by which models will be registered to one another 1304. In practice, models with greater overlap are registered to each other, then subsequent models are registered to the growing composite model. This maximizes the overlap between models at each registration step, increasing the reconstruction accuracy. The models comprising the series of individual three dimension topography models are then registered and stitched in a loop 1305 according to the calculated stitching order. Models u−1 1306 and u 1307 are registered to each other by using their calculated feature descriptions 1308 and 1309 to identify the subset of features in each model feature description common to both models, and computing and applying a transform 1310 from the model u to model u−1. An iterative closest points algorithm 1312 is then applied which optimizes coefficients derived from matching nearest neighbors in each model, using a coordinate space which includes X, Y, and Z three dimensional coordinates as well as color feature information as basis vectors. The stitched model then becomes model u−1, and the next model in the series according to the computed stitching order takes the role of model u. After registering all M models into a composite three dimensional topography model, additional iterations can be performed where each of the M models is compared to the composite model and it's position refined to minimize a weighting function. By tracking the weighting functions through successive iterations of looping through the M models, convergence can be determined. FIG. 14 depicts an example of the stitching process results for a series of measurement comprising three gaze directions. The flat-field illumination frames from the structured light pattern illumination measurements 1401, 1403, and 1405 are included to indicate the show direction of the eye relative to the imaging detector. The individual three dimensional topographical models resulting from the measurements at each gaze direction are displayed as 1402, 1404, and 1406. The final stitched composite three dimensional topographical model is shown in 1407.

In said embodiment the registration process efficiency and robustness is aided by accurate estimation of the gaze orientation vector prior to application of nearest neighbor techniques such as feature matching or iterative closest points algorithms. Accurate gaze estimation allows estimation of overlap regions between models, allowing search segmentation. Such gaze estimation is accomplished by identifying the corneal limbus by leveraging the contrast between the predominantly white sclera and the iris pigmentation. A plane can be fit to the three-dimensional limbus points, for example using a least squares criterion. The normal vector to the plane closely approximates the gaze orientation vector. The limbus plane is also used as a clipping plane to exclude features under the transparent corneal membrane, which are distorted by the optical properties of said corneal membrane, from the feature classification and matching algorithms.

In said embodiment speed and accuracy of the model registration process is enhanced by excluding all features not pertaining to the scleral surface from the feature classification and matching algorithms. A primary interfering feature is represented by eyelashes which protrude into the optical path of the imaging detector. When a valid camera-camera triangulation pair is present eyelashes can be identified by generating disparity maps based on images obtained during flat-field illumination of the eye during the measurement process.

In some embodiments, full three dimensional topographical models of the anterior ocular surface can be created either by manually retracting the lids of the eye to expose the entire portion of the ocular surface to be measured or by combining a plurality of individual three dimensional topography models each containing some segment of the entire portion of the ocular surface to be measured into a composite three dimensional topographical model of the anterior ocular surface. To produce the composite topographical model, the technology can operate in distinct modes: a Discrete Station Mode and a Continuous Processing Mode.

Figure 15:
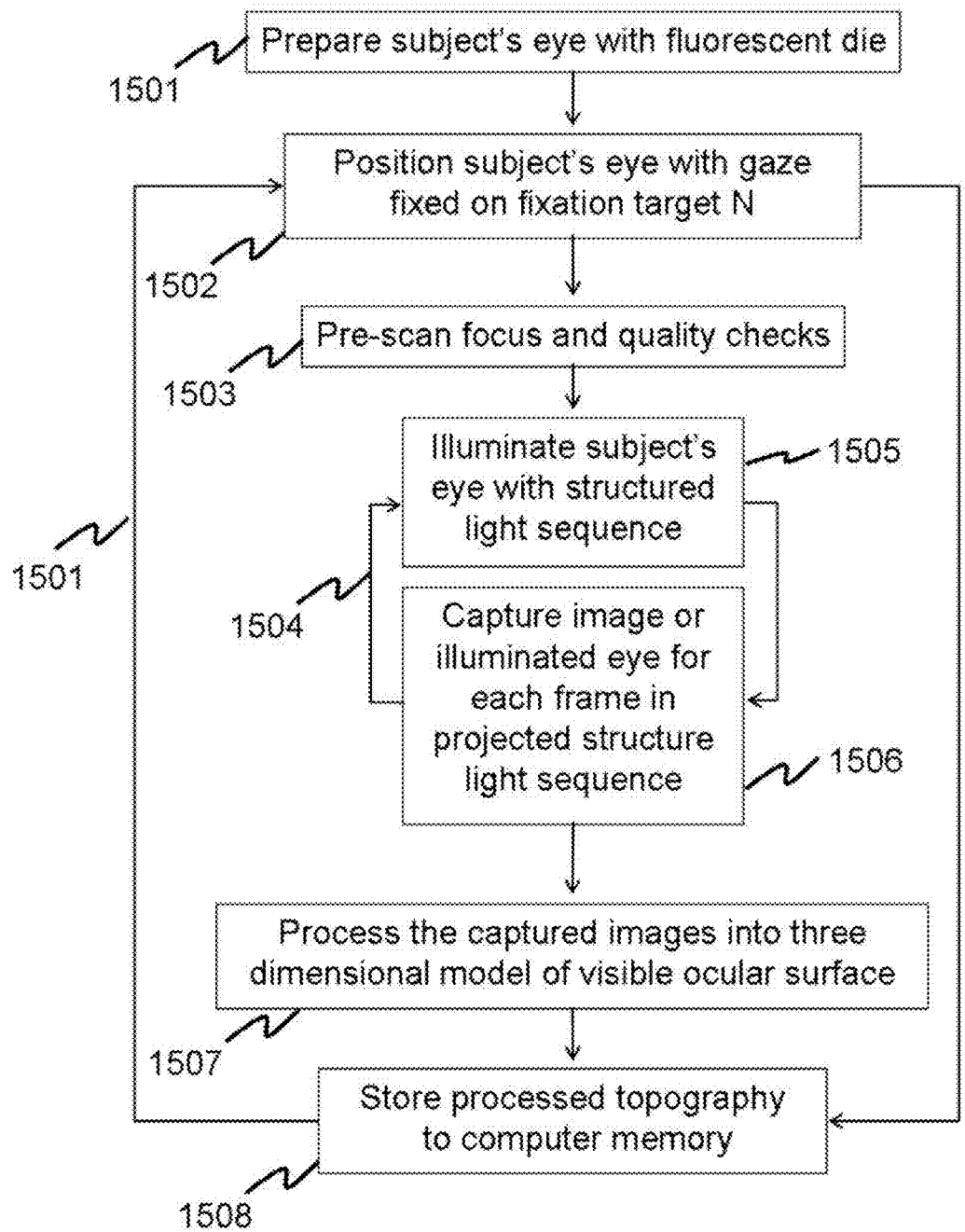
FIG. 15 is a flow chart depicting a sample iterative data acquisition process for operating in Discrete Station Mode.

When said embodiment is operating in Discrete Station Mode, the operation of the device is similar to the operation described previously and described in FIG. 9. In Discrete Station Mode, the steps 0902 through 0908 are operated in a loop where each iteration of the loop is realized by fixing gaze direction of the subject on a distinct element of the gaze fixation target array. The modified process is depicted in FIG. 15. The image sequence comprising the data from each measurement of the ocular surface is then processed into an individual three dimensional topographical model by the computing device, and the plurality of individual three dimensional topographical models are then combined into a composite model of the full extent of the anterior ocular surface portion measured.

When said embodiment is operating in Discrete Station Mode the locations of the elements in the gaze fixation target array are chosen such that the portion of the ocular surface measured when the gaze direction is fixed on element N−1 overlaps significantly with the portion of the ocular surface measured when the gaze direction is fixed on element N to allow optimal registration of individual models with respect to one another.

Figure 16:
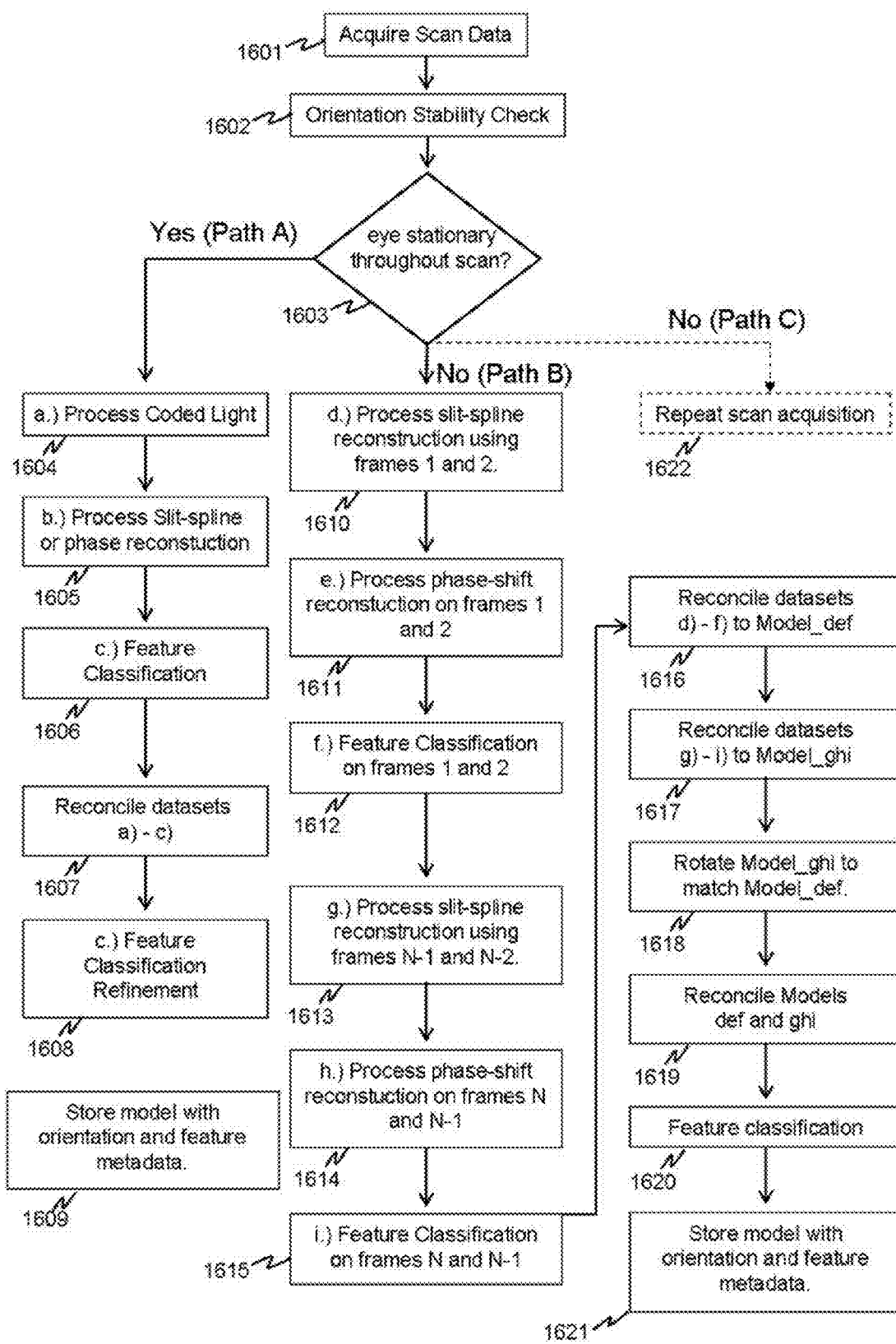
FIG. 16 is a flow chart depicting an example processing tree for Discrete Station Mode

FIG. 16 details the Discrete Station Mode processing tree. Scan data comprised of a sequence of images of the eye subject to a sequence of structured light patterns and flat-field illuminations is acquired for a given gaze direction 1601. A stability check 1602 is then performed by comparing flat-field illumination images comprising part of said pattern sequence and a stability metric is calculated. If the stability metric meets established criteria, the acquired data is processed through path A, including surface point triangulation by means of Coded-light reconstruction 1604 and Rasterstereographic reconstruction 1605. A preliminary feature classification is performed on each reconstruction result 1606, and weighting coefficients and surface constraints are applied to reconcile the various surface reconstructions 1607, before the flat-field illumination images are used in conjunction with SIFT and Block Match algorithms to create a detailed feature-based compliment to the three dimensional surface topology 1608 that is stored to the computer memory 1609 for future use.

If the stability metric 1602 fails to meet the established criteria, the data is processed through path B which uses a combination of slit-spline reconstruction 1610 square wave phase-shift reconstruction 1611 on individual image frames or pairs of image frames to mitigate the impact of eye motion by restricting the effective measurement windows to small fractions of the entire measurement window. A feature classification is then performed on each of the surface reconstructions 1612 using the flat-field illumination frame that preceded the structured light sequence. The process then repeats using last two frames or frame pairs in the structured light sequence in conjunction with the flat-field frame that follows the structured light sequence. Namely, frames N–1 and N of the structured light sequence are processed using the slit-spline 1613 and phase-shift reconstruction 1614 techniques and the feature classifications are performed using the flat-field frame 1615. The reconstruction results for Frames 1 and 2 are reconciled to each other using surface constraints and weighting coefficients 1616, and the same process is applied to the results for Frames N–2 and N–1, before the two reconciled results are combined and reconciled to one another 1618. A final feature classification step is performed to create the feature-based compliment 1620 and the topology and feature information are stored to the computer memory for future use 1621. In embodiments where flat-field illumination is acquired simultaneously with the structured light pattern illumination data by using color cameras and non-overlapping wavelength bands, each image frame or pair of image frames in the acquire data image sequence may be processed as a separate measurement into a separate individual three dimensional topography model with its own feature-based compliment as well, as opposed to processing only the beginning and end portions of the sequence.

An additional processing path for this embodiment operating in Discrete Station Mode is also available for real-time control of the measurement system hardware by the attached computing device. In said path C, if the stability metric fails to meet the established criteria, the data are re-acquired 1622.

When some embodiments are operating in Continuous Processing Mode, the data acquisition and data processing functions are directly coupled by means of the attached computing device to improve data quality and measurement speed. In Continuous Processing Mode, the gaze fixation target array is initialized by the computer, then the ocular surface is illuminated by a flat-field illumination frame and a structured light sequence truncated to one or a few frames of structured light patterns and image sequences of the illuminated ocular surface are captured by the imaging sensors. The computer processes the acquired image sequence into an individual three dimensional topography model with a feature-based compliment description, orientation vector, and model extents, then computes a desired gaze direction and updates the illumination of the gaze fixation target array. After each subsequent data acquisition, convergence, coverage, and quality metrics are calculated as part of the computation of the desired gaze direction for the next acquisition. This process continues until the calculated metrics meet established criteria, and the controlling computer algorithm ends the scan.

Figure 17:
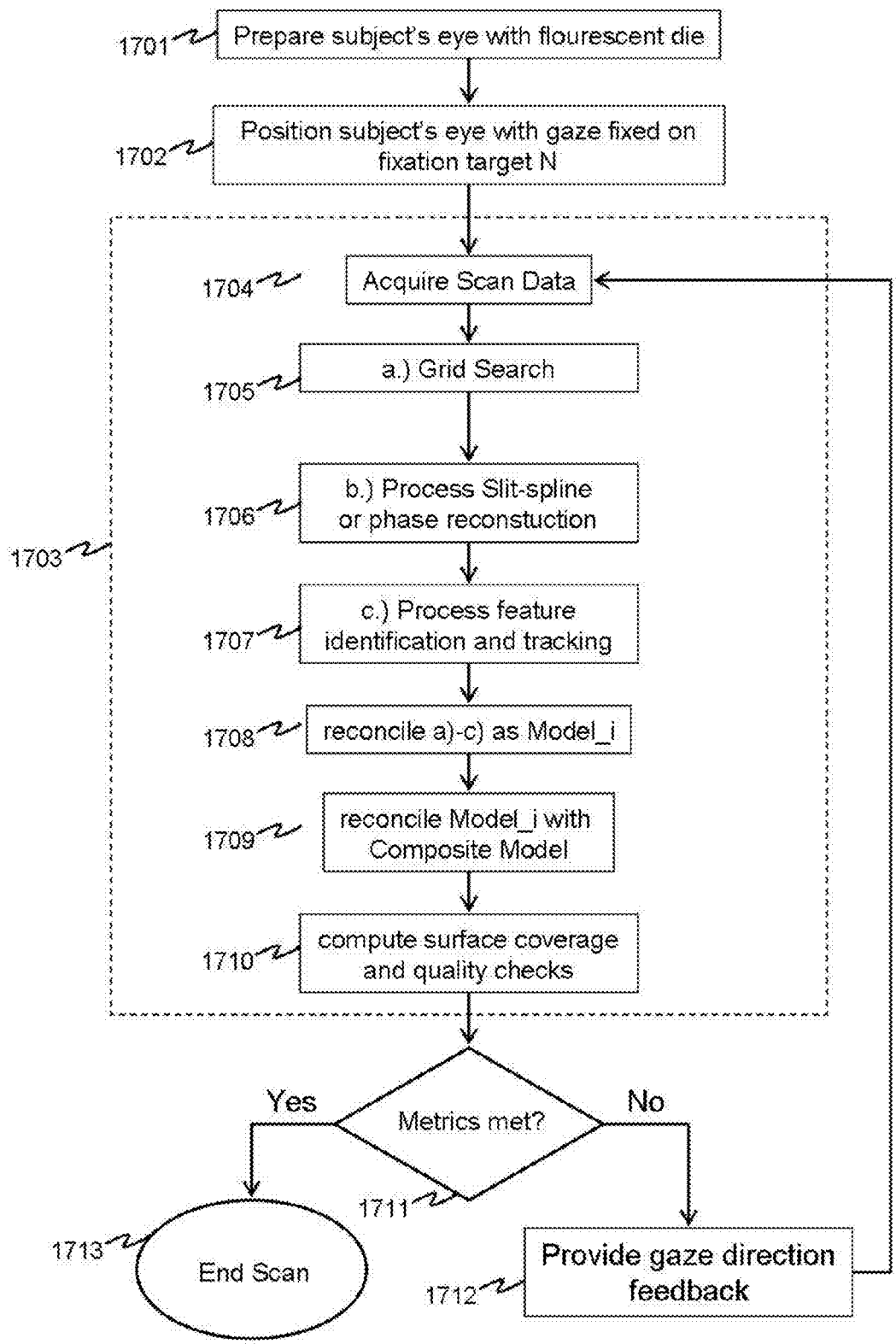
FIG. 17 is a flow chart depicting a sample measurement process for Operation of Continuous Processing Mode

The operation of Continuous Processing Mode for this embodiment is detailed in FIG. 17. The process begins with the subject's eye being prepared with fluorescent dye 1701 and fixed on the gaze fixation target array in its initial state 1702. The controlling algorithm enters the control loop 1703, during which it acquires image data by illuminating the eye with the structured light sequence and capturing images of the illuminate ocular surface 1704, processes the acquired image data using the Templated Grid Search algorithm 1705 and then applies one or both of Slit-spline reconstruction and square wave phase reconstruction 1706, computes the feature-based description compliment and the coverage and quality metrics 1707, and reconciles the topology and feature results 1708. For the first iteration of the loop, this reconciled topology and feature result becomes the composite model, for subsequent iterations of the loop, the composite model is updated through another reconciliation process with the newly measured components 1709. Coverage and quality metrics are then calculated 1710 and compared against established criteria 1711, after which a new gaze direction is determined and indicated on the fixation target array 1712, triggering the next scan iteration of the loop. For each measurement after the first, the new measurement is registered to the previous measurements by means of the feature-based registration stitching method described previously. The process repeats until the coverage and quality metrics meet the established convergence criteria.

In some embodiments, operating in Continuous Processing Mode offers speed and data quality improvements by providing real-time feedback on data quality and allowing the processing computer to correct for deficiencies in the acquired data during the initial measurement process, minimizing the possibility of repeating the measurement at a later time. For embodiments which take advantage of color imaging sensors, the data quality and speed are both improved significantly by simultaneous projection of the structured light pattern sequence and flat-field illumination frame using non-overlapping wavelength bands.

In some embodiments, a display screen attached to the computing device displays provides operational feedback to the user. This feedback includes real-time views of the acquired imagery for use in alignment and focusing of the measurement system with respect to the surface to be measured, intermediate stage progress indicators including focusing quality indicators, as well as visualizations of the three dimensional topographical models and optometrically useful realizations of said models and quantities derived from them.

Additional embodiments can be used to create a three dimensional model of the eye surface and electronically transmit it to the scleral and contact lens manufacturing facility for designing and building a custom lens that is specifically fit to a patient's eye.

Figure 18:
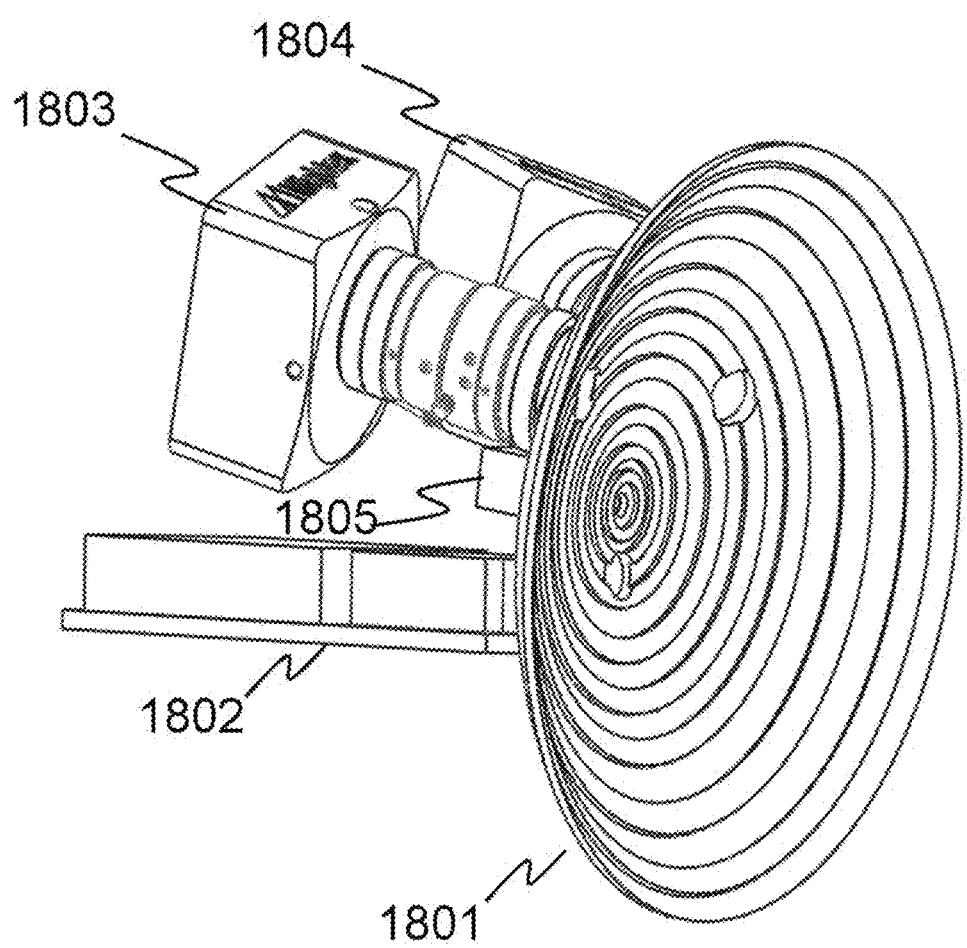
FIG. 18 is an illustration of one arrangement of an ocular topographer combining a Placido disk with a structured light system.

Both the system and method embodiments disclosed herein may be used independently or in can be combined with a Placido disk based corneal topography measurement within the same embodiment. In such embodiment, the traditional Placido disk measurement approach can be used to provide a rapid corneal measurement without the fluorescent substance, while the structured light system can be used for simultaneous measurement of the ocular surface measurement in the corneal and scleral regions. Measurements made by either approach may stand alone, may be registered into a common data set to complement one another, or may be incorporated as algorithmic constraints to one or both datasets to improve the accuracy of a single composite model of the ocular surface. A schematic drawing of the apparatus in a configuration allowing employment of both Placido disk and structured light stereo topographical measurement methods for ocular surface measurement is shown in FIG. 18, where the positions of the pattern projection system 1802 and the imaging detectors 1803 and 1804, analogous to the pattern projection system 0305 and imaging detectors 0301 and 0302 or the embodiment previously described, are modified so as to peer through openings in the Placido disk assembly 1801, so as not to interfere with the Placido disk's central imaging detector 1805. This can be done with minimal impact on the quality of the Placido disk measurement by choosing the openings in the Placido disk assembly to coincide with dark, non-illuminated regions of the disk assembly and by one-half-inch or other small diameter optical assemblies for the pattern projection system and the imaging detectors. In the apparatus depicted in FIG. 18a simultaneous measurement using Placido disk and structured light is possible in order to combine the two measurements to further increase the accuracy of the ocular surface measurement.

Some examples of the disclosure may have more than two cameras arranged in such fashion that more than three triangulation pairs can be created during the device operation and data analysis.

Additional Examples and Embodiments

In various embodiments, the systems and methods disclosed herein may achieve one, some, or all of the following advantages and/or provide some or all of the following functionality.

In some embodiments, three simultaneous independent measurements are used, which may advantageously provide error reduction in overlap regions through averaging, error reduction in overlap regions through constraints, wider field-of-view by having cameras out at angles to the surface to be measure, and/or more accurate tracking, because it may be difficult to use corneal points for tracking.

In some embodiments, coded structured light is used to map the surface of the object (e.g., the anterior surface of the eye). Pattern sequences can offer higher spatial resolution than single patterns, and unique pixel encoding can eliminate iterative point searching, which advantageously can increase speed and/or accuracy of the mapping.

In some implementations, multiple patterns may be avoided because of eye movements. Tracking and processing segmentation can allow for correction for eye movements. In some embodiments, trimming coded light bins to single stripes at bin edges can reduce dynamic range requirements and/or exposure modification requirements of the cameras. In some embodiments, trimming coded light sequence to moving set of identical patterns can provide processing flexibility. For example, with smoothness constraints for the surface, the systems can perform true coded light methods.

Various implementations may provide multiple processing techniques. For example, the techniques can include Standard Coded Light (e.g., using all frames or subset of frames), phase-shift or scanning slit using single frames, etc. The systems and methods can be implemented to allow selection between techniques based on eye stability. Multiple techniques to constrain solutions and improve surface accuracy can be adopted. In some embodiments, use of identical patterns means each frame, or any subset, can be processed by itself using alternate methods to battle eye movement during the mapping sequence.

In various implementations, a fluorescent dye can be applied to the object (e.g., the anterior surface of the eye) to deal with differences in surface reflectivities. In some embodiments, real-time brightness/quality indicator can be used to permit analysis of the dye coverage and fluorescence intensity during focusing or mapping, and optionally, after measurement. The systems and methods can be configured to warn if scans need to be repeated.

The disclosed focusing methods of the camera and projector geometry may allow a simple focusing/alignment indication by matching the projected focusing pattern with a fixed reference display pattern.

In some implementations, the measurements in multiple wavelengths allow obtaining position and intensity (e.g., XYZI) data. Such data may allow eye movement tracking, stitching registration of multiple partial datasets (e.g., using intensity domain features to constrain algorithms for stitching smooth surfaces, limbus detection for scleral lens fitting, and/or detection of problem spots such as scaring to avoid during scleral lens fitting.

In some implementations, simultaneous pattern projections in multiple wavelengths can be used. For example, flat field and structured light can be projected simultaneously. Red, green, blue (RGB) coded light is can be used in ophthalmic or non-ophthalmic settings.

In some applications, substantially the entire sclera can be mapped by moving the gaze direction, taking partial datasets, and then combining the datasets. In one example of a Discrete Station Mode, the systems and methods utilize discrete gaze directions and the processing starts from the XYZI models collected (including third party data). In one example of Continuous Processing Mode, the systems and methods utilize automated, guided data acquisition. The gaze direction moves around in field following an indicator directed by the algorithm until convergence is obtained.

In various implementations, any of the systems and methods disclosed herein can be combined with a Placido disk for two types of independent corneal measurements.

Additional Examples of Aspects of the Disclosure

In a first aspect, a system for measuring an anterior surface topography of an eye, the system comprising: a pattern projection system configured to emit light towards an ocular surface of the eye, wherein the pattern projection system is configured to project a sequence of patterns onto the ocular surface; one or more image sensors configured to record one or more images of the patterns resulting from the projected pattern sequence, an analysis system comprising computing hardware configured to determine a topographic map of the ocular surface from the one or more images of the patterns.

In a 2nd aspect, the system of aspect 1, wherein the patterns in the sequence are projected in a single wavelength band.

In a 3rd aspect, the system of aspect 1 or aspect 2, wherein the patterns in the sequence are projected in two or more wavelength bands.

In a 4th aspect, the system of any one of aspects 1-3, wherein one or more patterns in the projected sequence of patterns are emitted in a wavelength band at least partially overlapping an excitation wavelength of a fluorescent substance adapted to be applied to the eye.

In a 5th aspect, the system of any one of aspects 1-4, wherein one or more patterns in the projected sequence of patterns are emitted in a wavelength band not overlapping an excitation wavelength of a fluorescent substance adapted to be applied to the eye.

In a 6th aspect, the system of any one of aspects 1-5, wherein the pattern projection system is configured to produce structured light patterns in one or more of three modes which can be operated either simultaneously or sequentially, such that: in a first mode, an emitted wavelength range of the pattern projection system overlaps an excitation wavelength of a fluorescent substance used to prepare the ocular surface but does not overlap with a fluorescence wavelength of the fluorescent substance; in a second mode, an emitted wavelength range of the pattern projection system overlaps a fluorescence wavelength of a fluorescent substance used to prepare the ocular surface but does not overlap an excitation wavelength of the fluorescent substance; and in a third mode, an emitted wavelength range of the pattern projection system overlaps neither an excitation wavelength of a fluorescent substance used to prepare the ocular surface nor a fluorescence wavelength of the fluorescent substance.

In a 7th aspect, the system of any one of aspects 1-6, wherein the system is configured to perform a measurement of the ocular surface in a measurement duration less than about 0.5 seconds between the microsaccadic movements of the eye.

In an 8th aspect, the system of aspect 7, wherein the pattern projection system is configured to simultaneously project multiple individual patterns from the sequence of patterns in a coded light sequence, wherein each individual pattern is projected in a non-overlapping wavelength band.

In a 9th aspect, the system of aspect 8, wherein the one or more image sensors comprise a multi-color imaging detector configured to record each individual pattern in a separate recorded color channel, whereby system is configured to project and record the coded light sequence in one or more exposures.

In a 10th aspect, the system of any one of aspects 1-9, wherein illumination levels incident on the ocular surface are less than $3.9 \times 10^{-3}$ Joules of radiant energy as measured through a 7-mm aperture located within 5 mm of the projector focus.

In an 11th aspect, the system of any one of aspects 1-10, further comprising a fixation target system configured to permit a gaze of the eye to be sequentially fixed at a plurality of gaze directions.

In a 12th aspect, the system of aspect 11, wherein the fixation target system comprises one or both of: a plurality of targets to be illuminated in sequence or an emissive screen configured to display stationary or moving gaze fixation targets.

In a 13th aspect, the system of any one of aspects 1-12, further comprising a Placido disk corneal topographer system.

In a 14th aspect, the system of any one of aspects 1-13 wherein at least one of the one or more image sensors is configured to simultaneously record at least one of the one or more images in a plurality of wavelengths.

In a 15th aspect, the system of aspect 14, wherein the pattern projection system is configured to illuminate the ocular surface with a flat field in a first wavelength and one or more structured light patterns in second wavelength.

In a 16th aspect, the system of any one of aspects 1-15, further comprising a display device configured to display a representation of the topographic map of the ocular surface or a representation of one or more optometric values derived from the topographic map.

In a 17th aspect, the system of any one of aspects 1-16, further comprising a scleral contact lens manufacturing system, wherein the system is configured to communicate information related to the topographic map of the ocular surface to the scleral contact lens manufacturing system.

In an 18th aspect, a method for calculating a three-dimensional topographical model of an anterior ocular surface of an eye, the method comprising: under control of an ocular topographic mapping system comprising computer hardware: receiving images of projected structured light patterns that are reflected or emitted from the anterior ocular surface, the images obtained from a system comprising a plurality of imaging sensors configured to record images projected on the anterior ocular surface by a pattern projection system; analyzing the received images using one or more of the following techniques: coded light triangulation between any one of the plurality of imaging sensors and the pattern projection system, or rastersterographic triangulation between any two of the plurality of imaging sensors, slit-spline surface reconstruction, or phase-shift surface reconstruction; and determining, based at least in part on the analyzed images, a composite measurement of topography of at least a portion of the anterior ocular surface.

In a 19th aspect, the method of aspect 18, wherein determining the composite measurement of topography of at least a portion of the anterior ocular surface comprises combining a plurality of individual topography measurements of portions of the anterior surface of the eye taken at a plurality of orientations of an optical axis of the eye.

In a 20th aspect, the method of aspect 19, wherein each of the plurality of individual topography measurements is created from a series of images of projected structured light pattern sequences reflected from the anterior ocular surface, wherein each pattern sequence comprises: at least one image of the eye where the eye is illuminated in a wavelength range that overlaps a fluorescence wavelength of a fluorescent dye used to prepare the ocular surface but does not overlap an excitation wavelength of the fluorescent dye, and at least one projected structured light pattern where the projected pattern is illuminated in a wavelength range that overlaps the excitation wavelength of the fluorescent dye used to prepare the ocular surface but does not overlap the fluorescence wavelength of the fluorescent dye.

In a 21st aspect, the method of aspect 20, wherein determining the composite measurement of topography of at least a portion of the anterior ocular surface comprises: analyzing each of the plurality of individual topography measurements to provide a respective individual three-dimensional topographical model of a segment of the ocular surface, wherein the individual three-dimensional topographical model comprises three dimensional coordinate data, color intensity data, and a feature-based description of the individual three-dimensional topographical model produced from analyzing captured images of a reflected or a fluorescent pattern sequence.

In a 22nd aspect, the method of any one of aspects 19-21, wherein each of the plurality of individual topography measurements is taken in a Discrete Station Mode wherein an individual topography measurement is acquired with an optical axis of the eye directed at one of a plurality of fixed location fixation targets, wherein each individual topography measurement is created from a series of images of projected structured light pattern sequences reflected from the ocular surface, where each pattern sequence comprises: at least two flat-field images of the eye where the eye is illuminated in a wavelength range that overlaps a fluorescence wavelength of a fluorescent dye used to prepare the ocular surface but does not overlap an excitation wavelength of the fluorescent dye, and a sequence of at least one projected structured light pattern where the projected pattern is illuminated in wavelength range that overlaps the excitation wavelength of the fluorescent dye used to prepare the ocular surface but does not overlap the fluorescence wavelength of the fluorescent dye, and wherein at least one of the at least two flat-field images of the eye precedes the sequence of structured light patterns, and at least one of the at least two flat-field images of the eye follows the sequence of structured light patterns; and wherein the method further comprises processing each of the plurality of individual topography measurements into a respective individual three-dimensional topography model.

In a 23rd aspect, the method of aspect 22, further comprising analyzing at least one of the flat-field images which preceded the sequence of structured light patterns and at least one of the flat-field images which followed the structured light patterns to compute a metric describing apparent motion of the eye during a measurement period.

In a 24th aspect, the method of aspect 23, further comprising determining, based at least in part on the computed metric, at least one processing technique for constructing a respective individual three-dimensional topographical model.

In a 25th aspect, the method of any one of aspects 19-24, wherein each of the individual topography measurements is taken in Continuous Processing Mode wherein an individual topography measurement is acquired and processed in a continuous loop until a desired convergence metric or a time threshold is reached, the method further comprising: computing a composite three-dimensional topography model of the anterior ocular surface from combinations of individual three-dimensional topography measurements acquired during the continuous loop in a measurement window, while the orientation of the eye is allowed to change during the measurement window.

In a 26th aspect, the method of aspect 25, wherein each of the individual topography measurements taken in Continuous Processing Mode comprises: at least one flat-field image of the eye where the eye is illuminated by a wavelength range that overlaps the fluorescence wavelength of the fluorescent dye used to prepare the ocular surface but does not overlap the excitation wavelength of the fluorescent dye, and a sequence of at least one projected structured light patterns where the projected pattern is illuminated in a wavelength range that overlaps the excitation wavelength of the fluorescent dye used to prepare the ocular surface but does not overlap the fluorescence wavelength of the fluorescent dye, the method further comprising: projecting the at least one flat-field image and the sequence of at least one projected structured light patterns at least partially overlapped in time, if a color camera is used, or projecting the at least one flat-field image and the sequence of at least one projected structured light patterns sequentially, if a monochromatic cameras is used.

In a 27th aspect, the method of aspect 26, further comprising: processing each of the individual topography measurements into a rough individual three-dimensional topography along with extents and orientation of each rough individual three-dimensional topography model; combining each individual rough three-dimensional topography model with previous rough three-dimensional topography models taken during a measurement period of a subject into a rough composite three-dimensional topography model of a measured portion of the ocular surface; evaluating the extents and surface metrics of the measured portion of the ocular surface to provide a gauge of measurement quality and completeness; and communicating the measurements of quality and completeness in real time such that a gaze direction of the subject can be adjusted to facilitate completion of the measurement of the eye of the subject.

In a 28th aspect, the method of any one of aspects 18-27, wherein the projected structured light patterns comprise grids of parallel lines or square wave patterns.

In a 29th aspect, the method of any one of aspects 18-28 wherein the projected structured light patterns are chosen to minimize frame-to-frame variation of incident intensity of illumination striking the ocular surface.

In a 30th aspect, the method of any one of aspects 18-29, wherein the one or more of the following techniques comprise at least two of the techniques, and the at least two techniques are applied to constrain or refine the composite measurement of topography.

In a 31st aspect, the method of any one of aspects 18-30, further comprising: analyzing received images of reflected flat-field illumination to compute a feature-based description of individual three-dimensional topographical models of the measured portion of the ocular surface for registering the individual three-dimensional topographical models in Cartesian space; and analyzing, based at least in part on the feature-based description, rotation and translation of an individual three-dimensional topographical model with respect to another individual three-dimensional topographical model or with respect to that same individual three-dimensional topographical model over the course of the measurement.

In a 32nd aspect, the method of aspect 31, wherein the feature-based description contains points which correspond to the corneal limbus of the eye, the method further comprising creating a masking region which excludes non-topographical features in the corneal region from the feature-based description of the individual three-dimensional topographical models to prevent optical properties of the cornea from skewing the analysis of the rotation and translation of an individual three-dimensional topographical model, and wherein a plane-fit to the corneal limbus points is used to determine an approximate orientation for the optical axis of the eye.

In a 33rd aspect, the method of any one of aspects 18-32, further comprising: receiving flat-field images captured simultaneously on more than one of the plurality of imaging sensors; and determining regions of the images that are occluded in one or more received image by protruding eyelashes.

Although descriptions of the embodiments herein have focused on measurement of the anterior surface of the human or animal eye, some embodiments of the technology may be equally applicable to the measurement of surfaces of other objects of biologic or non-biologic nature.

The presence of broadening words and phrases such as "one or more," "at least," "but not limited to" or other like phrases in some instances shall not be read to mean that the narrower case is intended or required in instances where such broadening phrases may be absent. The use of the term "optical measurement head" does not imply that the components or functionality described or claimed as part of the optical measurement head are all configured in a common package. Indeed, any or all of the various components of an optical measurement head, whether control logic or other components, can be combined in a single package or separately maintained and can further be distributed in multiple groupings or packages or across multiple locations.

Additionally, the various embodiments set forth herein are described in terms of example block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

While various embodiments of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Each of the processes, methods, and algorithms described herein and/or depicted in the attached figures may be embodied in, and fully or partially automated by, code modules executed by one or more physical computing systems, computer processors, application-specific circuitry, and/or electronic hardware configured to execute computer instructions. For example, computing systems can include general purpose computers configured with specific executable instructions for performing the disclosed methods or special purpose computers, servers, desktop computers, laptop or notebook computers or tablets, personal mobile computing devices, mobile telephones, and so forth. A code module may be stored in non-transitory computer memory, compiled and linked into an executable program, installed in a dynamic link library, or may be written in an interpreted programming language. Further, certain implementations of the functionality of the present disclosure are sufficiently mathematically, computationally, or technically complex that application-specific hardware or one or more physical computing devices (utilizing appropriate executable instructions) may be necessary to perform the functionality, for example, due to the volume or complexity of the calculations involved (e.g., computing ocular topography) or to provide results substantially in real-time.

Code modules may be stored on any type of non-transitory computer-readable medium, such as physical computer storage including hard drives, solid state memory, random access memory (RAM), read only memory (ROM), optical disc, volatile or non-volatile storage, combinations of the same and/or the like. The methods and modules may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes and process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities can be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto can be performed in other sequences that are appropriate, for example, in serial, in parallel, or in some other manner. Tasks or events may be added to or removed from the disclosed example embodiments. Moreover, the separation of various system components in the implementations described herein is for illustrative purposes and should not be understood as requiring such separation in all implementations. It should be understood that the described program components, methods, and systems can generally be integrated together in a single computer or software product or packaged into multiple computer or software products. Many implementation variations are possible.

The processes, methods, and systems may be implemented in a network (or distributed) computing environment. Network environments include enterprise-wide computer networks, intranets, local area networks (LAN), wide area networks (WAN), personal area networks (PAN), cloud computing networks, crowd-sourced computing networks, the Internet, and the World Wide Web. The network may be a wired or a wireless network (e.g., a terrestrial and/or satellite network) or any other type of communication network.

The various elements, features and processes described herein may be used independently of one another, or may be combined in various ways. All possible combinations and subcombinations are intended to fall within the scope of this disclosure. Further, nothing in the foregoing description is intended to imply that any particular feature, element, component, characteristic, step, module, method, process, task, or block is necessary or indispensable. The example systems and components described herein may be configured differently than described. For example, elements or components may be added to, removed from, or rearranged compared to the disclosed examples.

As used herein any reference to "one embodiment" or "some embodiments" or "an embodiment" means that a particular element, feature, structure, or characteristic described in connection with the embodiment is included in at least one embodiment. The appearances of the phrase "in one embodiment" in various places in the specification are not necessarily all referring to the same embodiment. Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. In addition, the articles "a" or "an" as used in this application and the appended claims are to be construed to mean "one or more" or "at least one" unless specified otherwise.

As used herein, the terms "comprises," "comprising," "includes," "including," "has," "having" or any other variation thereof, are open-ended terms and intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), or both A and B are true (or present). As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present disclosure should not be limited by any of the above-described exemplary embodiments.

What is claimed is:

1. A system for measuring an anterior surface topography of an eye, the system comprising:
   a pattern projection system configured to emit light towards an ocular surface of the eye, wherein the pattern projection system is configured to project a sequence of patterns onto the ocular surface;
   one or more image sensors configured to record one or more images of the patterns resulting from the projected pattern sequence,
   an analysis system comprising computing hardware configured to determine a topographic map of the ocular surface from the one or more images of the patterns.

2. The system of claim 1, wherein the patterns in the sequence are projected in a single wavelength band.

3. The system of claim 1, wherein the patterns in the sequence are projected in two or more wavelength bands.

4. The system of claim 1, wherein one or more patterns in the projected sequence of patterns are emitted in a wavelength band at least partially overlapping an excitation wavelength of a fluorescent substance adapted to be applied to the eye.

5. The system of claim 1, wherein one or more patterns in the projected sequence of patterns are emitted in a wavelength band not overlapping an excitation wavelength of a fluorescent substance adapted to be applied to the eye.

6. The system of claim 1, wherein the pattern projection system is configured to produce structured light patterns in one or more of three modes which can be operated either simultaneously or sequentially, such that:
   in a first mode, an emitted wavelength range of the pattern projection system overlaps an excitation wavelength of a fluorescent substance used to prepare the ocular surface but does not overlap with a fluorescence wavelength of the fluorescent substance;
   in a second mode, an emitted wavelength range of the pattern projection system overlaps a fluorescence wavelength of a fluorescent substance used to prepare the ocular surface but does not overlap an excitation wavelength of the fluorescent substance; and
   in a third mode, an emitted wavelength range of the pattern projection system overlaps neither an excitation wavelength of a fluorescent substance used to prepare the ocular surface nor a fluorescence wavelength of the fluorescent substance.

7. The system of claim 1, wherein the system is configured to perform a measurement of the ocular surface in a measurement duration less than about 0.5 seconds between the microsaccadic movements of the eye.

8. The system of claim 7, wherein the pattern projection system is configured to simultaneously project multiple individual patterns from the sequence of patterns in a coded light sequence, wherein each individual pattern is projected in a non-overlapping wavelength band.

9. The system of claim 8, wherein the one or more image sensors comprise a multi-color imaging detector configured to record each individual pattern in a separate recorded color channel, whereby system is configured to project and record the coded light sequence in one or more exposures.

10. The system of claim 1, wherein illumination levels incident on the ocular surface are less than $3.9 \times 10^{-3}$ Joules of radiant energy as measured through a 7-mm aperture located within 5 mm of the projector focus.

11. The system of claim 1, further comprising a fixation target system configured to permit a gaze of the eye to be sequentially fixed at a plurality of gaze directions.

12. The system of claim 11, wherein the fixation target system comprises one or both of: a plurality of targets to be illuminated in sequence or an emissive screen configured to display stationary or moving gaze fixation targets.

13. The system of claim 1, further comprising a placido disk corneal topographer system.

14. The system of claim 1 wherein at least one of the one or more image sensors is configured to simultaneously record at least one of the one or more images in a plurality of wavelengths.

15. The system of claim 14, wherein the pattern projection system is configured to illuminate the ocular surface with a flat field in a first wavelength and one or more structured light patterns in second wavelength.

16. The system of claim 1, further comprising a display device configured to display a representation of the topographic map of the ocular surface or a representation of one or more optometric values derived from the topographic map.

17. The system of claim 1, further comprising a scleral contact lens manufacturing system, wherein the system is configured to communicate information related to the topographic map of the ocular surface to the scleral contact lens manufacturing system.

18. A method for calculating a three-dimensional topographical model of an anterior ocular surface of an eye, the method comprising:
   under control of an ocular topographic mapping system comprising computer hardware:
   receiving images of projected structured light patterns that are reflected or emitted from the anterior ocular surface, the images obtained from a system comprising a plurality of imaging sensors configured to record images projected on the anterior ocular surface by a pattern projection system;
   analyzing the received images using one or more of the following techniques:

coded light triangulation between any one of the plurality of imaging sensors and the pattern projection system, or rastersterographic triangulation between any two of the plurality of imaging sensors, slit-spline surface reconstruction, or phase-shift surface reconstruction; and determining, based at least in part on the analyzed images, a composite measurement of topography of at least a portion of the anterior ocular surface.

19. The method of claim 18, wherein determining the composite measurement of topography of at least a portion of the anterior ocular surface comprises combining a plurality of individual topography measurements of portions of the anterior surface of the eye taken at a plurality of orientations of an optical axis of the eye.

20. The method of claim 19, wherein each of the plurality of individual topography measurements is created from a series of images of projected structured light pattern sequences reflected from the anterior ocular surface, wherein each pattern sequence comprises:

at least one image of the eye where the eye is illuminated in a wavelength range that overlaps a fluorescence wavelength of a fluorescent dye used to prepare the ocular surface but does not overlap an excitation wavelength of the fluorescent dye, and at least one projected structured light pattern where the projected pattern is illuminated in a wavelength range that overlaps the excitation wavelength of the fluorescent dye used to prepare the ocular surface but does not overlap the fluorescence wavelength of the fluorescent dye.

21. The method of claim 20, wherein determining the composite measurement of topography of at least a portion of the anterior ocular surface comprises:

analyzing each of the plurality of individual topography measurements to provide a respective individual three-dimensional topographical model of a segment of the ocular surface, wherein the individual three-dimensional topographical model comprises three dimensional coordinate data, color intensity data, and a feature-based description of the individual three-dimensional topographical model produced from analyzing captured images of a reflected or a fluorescent pattern sequence.

22. The method of claim 19, wherein each of the plurality of individual topography measurements is taken in a discrete station mode wherein an individual topography measurement is acquired with an optical axis of the eye directed at one of a plurality of fixed location fixation targets, wherein each individual topography measurement is created from a series of images of projected structured light pattern sequences reflected from the ocular surface, where each pattern sequence comprises:

at least two flat-field images of the eye where the eye is illuminated in a wavelength range that overlaps a fluorescence wavelength of a fluorescent dye used to prepare the ocular surface but does not overlap an excitation wavelength of the fluorescent dye, and a sequence of at least one projected structured light pattern where the projected pattern is illuminated in wavelength range that overlaps the excitation wavelength of the fluorescent dye used to prepare the ocular surface but does not overlap the fluorescence wavelength of the fluorescent dye, and wherein at least one of the at least two flat-field images of the eye precedes the sequence of structured light patterns, and at least one of the at least two flat-field images of the eye follows the sequence of structured light patterns; and wherein the method further comprises processing each of the plurality of individual topography measurements into a respective individual three-dimensional topography model.

23. The method of claim 22, further comprising analyzing at least one of the flat-field images which preceded the sequence of structured light patterns and at least one of the flat-field images which followed the structured light patterns to compute a metric describing apparent motion of the eye during a measurement period.

24. The method of claim 23, further comprising determining, based at least in part on the computed metric, at least one processing technique for constructing a respective individual three-dimensional topographical model.

25. The method of claim 19, wherein each of the individual topography measurements is taken in continuous processing mode wherein an individual topography measurement is acquired and processed in a continuous loop until a predetermined convergence metric or a time threshold is reached, the method further comprising:

computing a composite three-dimensional topography model of the anterior ocular surface from combinations of individual three-dimensional topography measurements acquired during the continuous loop in a measurement window, while the orientation of the eye is allowed to change during the measurement window.

26. The method of claim 25, wherein each of the individual topography measurements taken in continuous processing mode comprises:

at least one flat-field image of the eye where the eye is illuminated by a wavelength range that overlaps the fluorescence wavelength of the fluorescent dye used to prepare the ocular surface but does not overlap the excitation wavelength of the fluorescent dye, and a sequence of at least one projected structured light patterns where the projected pattern is illuminated in a wavelength range that overlaps the excitation wavelength of the fluorescent dye used to prepare the ocular surface but does not overlap the fluorescence wavelength of the fluorescent dye, the method further comprising:

projecting the at least one flat-field image and the sequence of at least one projected structured light patterns at least partially overlapped in time, if a color camera is used, or projecting the at least one flat-field image and the sequence of at least one projected structured light patterns sequentially, if a monochromatic cameras is used.

27. The method of claim 26, further comprising:

processing each of the individual topography measurements into a rough individual three-dimensional topography along with extents and orientation of each rough individual three-dimensional topography model;

combining each individual rough three-dimensional topography model with previous rough three-dimensional topography models taken during a measurement period of a subject into a rough composite three-dimensional topography model of a measured portion of the ocular surface;

evaluating the extents and surface metrics of the measured portion of the ocular surface to provide a gauge of measurement quality and completeness; and communicating the measurements of quality and completeness in real time such that a gaze direction of the subject can be adjusted to facilitate completion of the measurement of the eye of the subject.

28. The method of claim 18, wherein the projected structured light patterns comprise grids of parallel lines or square wave patterns.

29. The method of claim 18 wherein the projected structured light patterns are chosen to minimize frame-to-frame variation of incident intensity of illumination striking the ocular surface.

30. The method of claim 18, wherein the one or more of the following techniques comprise at least two of the techniques, and the at least two techniques are applied to constrain or refine the composite measurement of topography.

31. The method of claim 18, further comprising:
analyzing received images of reflected flat-field illumination to compute a feature-based description of individual three-dimensional topographical models of the measured portion of the ocular surface for registering the individual three-dimensional topographical models in cartesian space; and
analyzing, based at least in part on the feature-based description, rotation and translation of an individual three-dimensional topographical model with respect to another individual three-dimensional topographical model or with respect to that same individual three-dimensional topographical model over the course of the measurement.

32. The method of claim 31, wherein the feature-based description contains points which correspond to the corneal limbus of the eye, the method further comprising creating a masking region which excludes non-topographical features in the corneal region from the feature-based description of the individual three-dimensional topographical models to prevent optical properties of the cornea from skewing the analysis of the rotation and translation of an individual three-dimensional topographical model, and wherein a plane-fit to the corneal limbus points is used to determine an approximate orientation for the optical axis of the eye.

33. The method of claim 18, further comprising:
receiving flat-field images captured simultaneously on more than one of the plurality of imaging sensors; and
determining regions of the images that are occluded in one or more received image by protruding eyelashes.

* * * * *